US012773297B1

(12) United States Patent
Groscurth et al.

(10) Patent No.: US 12,773,297 B1
(45) Date of Patent: Oct. 27, 2026

(54) SEQUENTIAL DENTAL SURGICAL GUIDE AND MODEL SYSTEM AND METHOD

(71) Applicant: Clayton Dental Laboratory, Inc., Troy, MI (US)

(72) Inventors: Randall C. Groscurth, Troy, MI (US); Shoko U. Groscurth, Troy, MI (US)

(73) Assignee: Clayton Dental Laboratory, Inc., Troy, MI (US)

( * ) Notice: Subject to any disclaimer, the term of this patent is extended or adjusted under 35 U.S.C. 154(b) by 0 days.

(21) Appl. No.: 19/291,103

(22) Filed: Aug. 5, 2025

Related U.S. Application Data

(60) Provisional application No. 63/706,945, filed on Oct. 14, 2024, provisional application No. 63/679,430, filed on Aug. 5, 2024.

(51) Int. Cl.

| | |
|---|---|
| ***A61C 1/08*** | (2006.01) |
| ***A61B 17/16*** | (2006.01) |
| ***A61C 8/00*** | (2006.01) |
| ***A61C 13/34*** | (2006.01) |

(52) U.S. Cl.
CPC .......... *A61C 1/084* (2013.01); *A61B 17/1673* (2013.01); *A61C 8/0095* (2013.01); *A61C 13/34* (2013.01)

(58) Field of Classification Search
CPC ....... A61C 1/084; A61C 8/0095; A61C 13/34; A61B 17/1673
USPC ........................................................... 433/75
See application file for complete search history.

(56) References Cited

U.S. PATENT DOCUMENTS

| | | | |
|---|---|---|---|
| 4,917,604 | A | 4/1990 | Small |
| 5,221,204 | A | 6/1993 | Kruger et al. |
| 5,641,289 | A | 6/1997 | Sussman |
| 6,672,870 | B2 | 1/2004 | Knapp |
| 8,630,869 | B2 | 1/2014 | Royal et al. |
| 9,226,801 | B2 | 1/2016 | Groscurth et al. |
| 9,283,055 | B2 | 3/2016 | Thompson, Jr. et al. |
| 9,504,533 | B2 | 11/2016 | Groscurth et al. |
| 9,848,965 | B2 | 12/2017 | Kim et al. |
| 10,363,115 | B2 | 7/2019 | Groscurth et al. |
| 11,234,791 | B2 | 2/2022 | Groscurth et al. |
| 11,779,434 | B2 | 10/2023 | Jusuf et al. |
| 11,806,209 | B2 | 11/2023 | Watson |
| 11,980,510 | B2 | 5/2024 | Llop et al. |
| 12,042,345 | B2 | 7/2024 | Watson |
| 12,076,199 | B2 | 9/2024 | Groscurth et al. |

(Continued)

OTHER PUBLICATIONS

Freyer et al, Method for Producing a Treatment Jig, WO-2009056397-A1, machine translation (Year: 2009).*

(Continued)

*Primary Examiner* — Eric J Rosen
*Assistant Examiner* — Mirayda A Aponte
(74) *Attorney, Agent, or Firm* — Hayes Soloway P.C.

(57) ABSTRACT

A dental surgical guide set includes at least one fixation element. Each fixation element is independently capable of fixation to an oral structure. The dental surgical guide set includes a dental appliance having at least one fixation connector integral therewith removably engageable with the at least one fixation element after the fixation element is fixed to the oral structure. Engagement of the at least one fixation element and the at least one fixation connector fixes the dental appliance against the oral structure.

20 Claims, 23 Drawing Sheets

(56) References Cited

U.S. PATENT DOCUMENTS

| | | | | |
|---|---|---|---|---|
| 2004/0043355 | A1 | 3/2004 | Jonsson et al. | |
| 2005/0080503 | A1 | 4/2005 | Kopelman et al. | |
| 2006/0115793 | A1 | 6/2006 | Kopelman et al. | |
| 2006/0223029 | A1 | 10/2006 | Berger | |
| 2008/0124676 | A1 * | 5/2008 | Marotta | A61C 1/084 433/221 |
| 2008/0166681 | A1 | 7/2008 | Weinstein et al. | |
| 2009/0042167 | A1 | 2/2009 | Van Der Zel | |
| 2009/0298009 | A1 | 12/2009 | Brajnovic | |
| 2010/0004698 | A1 | 1/2010 | De Moyer | |
| 2010/0190137 | A1 | 7/2010 | Hertz | |
| 2010/0203479 | A1 | 8/2010 | Bulloch et al. | |
| 2015/0010881 | A1 | 1/2015 | Llop | |
| 2016/0278878 | A1 | 9/2016 | Watson et al. | |
| 2024/0216105 | A1 | 7/2024 | Groscurth et al. | |
| 2024/0374346 | A1 | 11/2024 | Groscurth et al. | |

OTHER PUBLICATIONS

Romain Lan, "Current Knowledge About Stackable Guides: A Scoping Review", 2024, Journal, 1-35, vol. 10, No. 28, International Journal of Implant Dentistry.

* cited by examiner

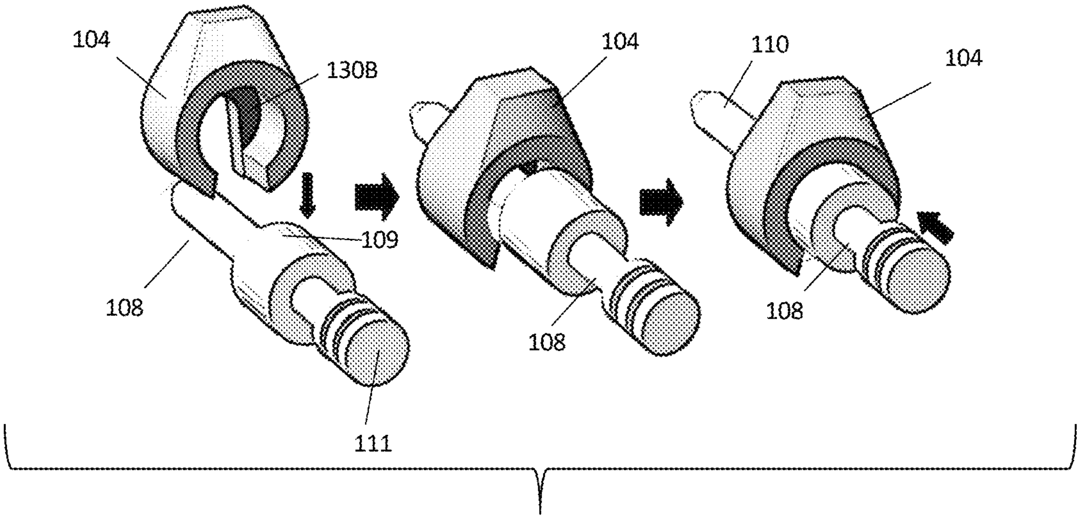
FIG. 8
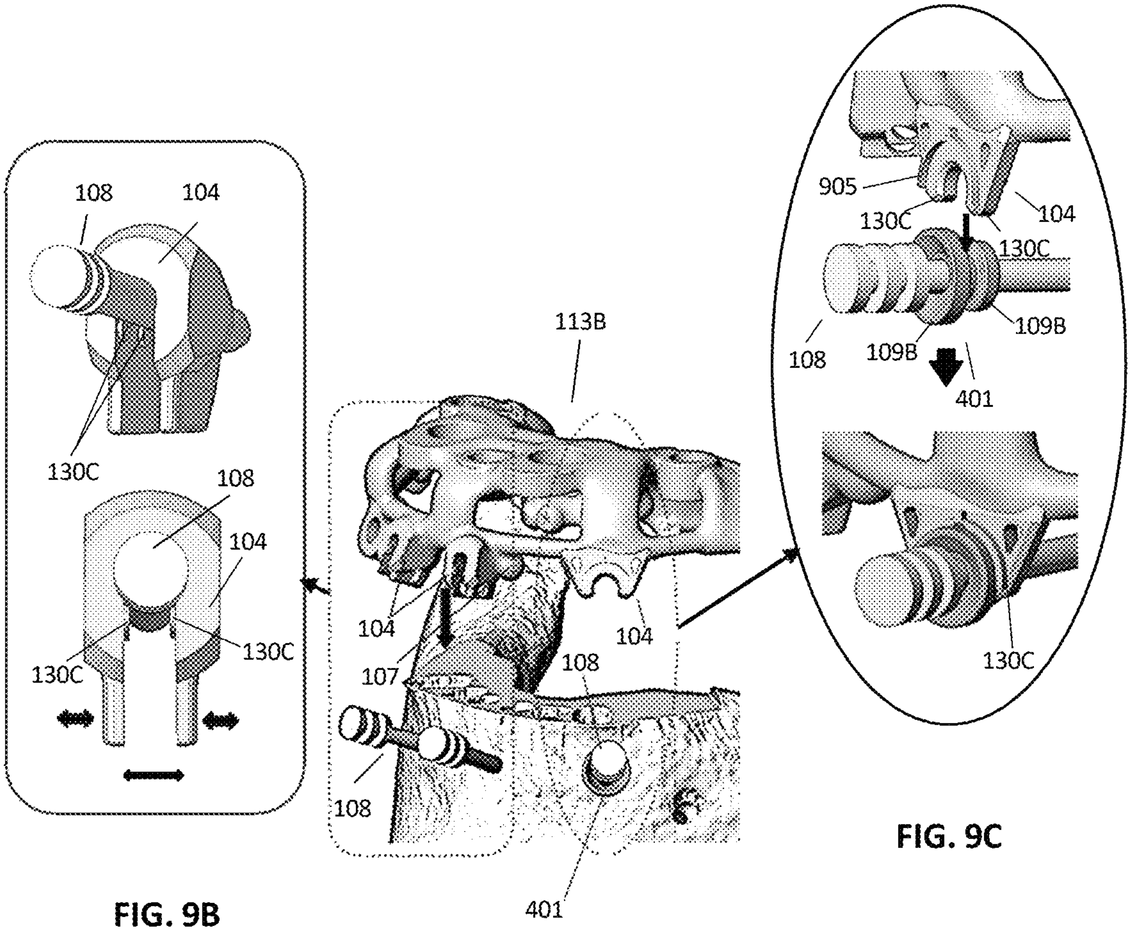
FIG. 9B
FIG. 9C
FIG. 9A

SEQUENTIAL DENTAL SURGICAL GUIDE AND MODEL SYSTEM AND METHOD

CROSS-REFERENCE TO RELATED APPLICATIONS AND PRIORITY

Provisional application this patent application claims priority from U.S. Provisional Patent Application No. 63/679,430 filed Aug. 5, 2024 and U.S. Provisional Patent Application No. 63/706,945 filed Oct. 14, 2024. Each of these patent applications are herein incorporated by reference in their entirety.

FIELD OF INVENTION

An improved apparatus set and method for full mouth rehabilitation procedures for dental implant cases is disclosed, and more particularly, dental implant surgical guide set, master implant model making kit, and temporary or final implant restoration and related method.

BACKGROUND

For full mouth implant surgeries that require bone reduction especially for the cases that need extraction of all remaining dentition, creating a well-fitting surgical guide is a challenge. One solution is a sequential type of surgical guide set that includes a fixation site drill guide fit to remaining teeth of a patient for drilling just fixation sites and possibly for marking the planned bone reduction level on the facial side of jawbone and surgical drill to drill osteotomies for implants. It may also include a dental restoration for immediate loading. This type of surgical guide system was described in U.S. patent application Ser. No. 15/044,979 (Watson et. al.). The biggest problem with this type of guide system was the difficulty of finding the drilled fixation holes to place fixation pins every time the surgeon needs to replace the guide appliance to move on to the next step of the surgery. To solve this problem, Watson suggested that one extra hole can be drilled with the fixation site drill guide on the facial side of the jawbone for inserting a pin so that it can be used as a fiducial marker for positioning a surgical guide which has a notch to be aligned with the pin. However, one pin operates inadequately as a fiducial marker to position the surgical guide accurately after extraction of all remaining teeth and losing one potential fixation location to a fiducial marker increases the difficulty of finding fixation site locations with many full mouth cases. Moreover, the difficulty of removing the fixation pins and reinserting them into the fixation holes remains when exchanging guide appliances (and a dental restoration).

Another solution is a stackable type of drill guide system introduced in US 9,504,533 (Groscurth, et. Al). This guide set may include a positioning attachment, a base frame, surgical drill guide, modified denture attachment, etc. The base frame can be positioned on a patient's oral structure, aided by the positioning attachment and fixation sites are drilled through drill guide holes on the base frame for fixating the base frame to the oral structure. After the positioning attachment is removed from the base frame, the base frame can be used as a bone reduction jig, if required. Then surgical drill guide can be attached to the base frame and osteotomies are drilled for planned implant sites. The advantage of this system is that, once the base frame is fixated to the oral structure, multiple guide appliances can be attached to the base frame one after another to aid different stages of surgical procedure. If immediate loading is planned, it can be done easily by designing a dental restoration (modified denture) as a super structure. However, this type of system has some disadvantages. Since the guide set requires assembly of stackable parts, the designing process is more complicated, and the fitting of each parts needs to be checked carefully. If the base frame and all substructures are made with plastic and have enough rigidity, the guide assembly may become too bulky in mouth. The solution to this is to make the base frame with metal, but metal frames make the production process more technically involved, and more expensive to manufacture. Many dental practitioners have 3D printers in their own offices and print surgical drill guides designed by remotely located dental laboratories, which is not presently conducive to metal frames. For these reasons, stackable guide sets remain a challenge.

Even though the stackable guide system can be useful, it is desirable to provide an alternative drill guide system that is less expensive, less technically involved, more compact and suitable for remote manufacturing in regular dental offices.

BRIEF SUMMARY OF THE INVENTION

Accordingly, an object of the disclosed invention is to provide a solution suited for the new era of digital dentistry and remote manufacturing with an improved surgical guide set, to improve functionality of each appliance in the guide set, and to create an implant model system that realize smooth and easy surgical workflow up to the creation of a final dental restoration. A dental surgical guide set includes at least one fixation element. Each fixation element is independently capable of fixation to an oral structure of a patient. The dental surgical guide set includes a dental appliance having at least one fixation connector removably engageable with the at least one fixation element after the fixation element is fixed to the oral structure. Engagement of the at least one fixation element and the at least one fixation connector fixes the dental appliance against the oral structure.

One embodiment of the invention includes a surgical guide set with a series of dental appliances with one or more open-face connectors detachably attachable and lockable to one or more fixation pins inserted to pre-planned locations of a patient's oral structure so that multiple guide appliances for aiding different stages of the surgical procedure and a dental restoration can be properly positioned on the patient's oral structure without removing fixation pins working as fiducial markers. For such dental appliances, various types of alternative locking system for open-face connectors are contemplated and disclosed, which includes fixation pins/screws with locking mechanism, drill guide sleeves with locking mechanism, and external locking rings.

In various embodiments, the surgical guide set may comprise at least two of the following dental appliances that were designed based on patient's preoperative data set: a fixation site drill guide, a bone reduction jig, a surgical drill guide, a timing jig for implants or implant abutments, a dental restoration, a dental restoration base, a transfer jig for physical transferring or digital transferring of positioning index of installed implants, a dental model base. Variations of designs and features for the appliances are also disclosed.

In embodiments, the surgical guide set may comprise guide appliances with one or more extra drill guide hole(s) for creating one or more recessed holes. Also disclosed are the methods of how to position and/or stabilize a guide appliance and/or a dental restoration by inserting positioning posts on the device or detachably attachable positioning pins.

In embodiments, the surgical guide set may comprise a dental restoration with a peelable restoration base made of a material with elasticity. The restoration assembly can be positioned on the oral structure using the positioning post(s) and/or the open-face connector(s).

In embodiments, the surgical guide set may comprise a post operative model system that provides easy workflow from transferring positional index of installed implants to creation of the final restoration using a unique connector system and is alignable to the pre-operative master data file based on which the appliances and the model base are designed. Variations of model designs and connections are also disclosed.

In another embodiment, the model system, locking pin system and other disclosed features can be applied to a stackable type of guide system.

BRIEF DESCRIPTION OF THE DRAWINGS

FIG. 8 is a perspective view of a series of steps to engage a fixation element with a fixation connector.

FIG. 9A is a perspective view of a surgical drill guide with other two different exemplary fixation connectors illustrated as being lowered onto an oral structure with fixation elements fixed to the oral structure.

FIG. 9B is a perspective view and a front elevational view of a fixation element engaged in a snap-fit with a first type of the exemplary fixation connectors.

FIG. 9C is partial side perspective views of the second type of fixation connector engaging with a drill guide sleeve having a fixation element.

DETAILED DESCRIPTION AND BEST MODE OF IMPLEMENTATION

Figure 1A:
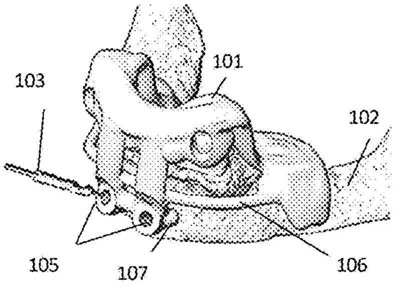
FIG. 1A is a perspective view of a fixation site drill guide placed on an oral structure and a drill bit aligned to a fixation site.

Referring now to the discussion that follows and also to the drawings, illustrative approaches are shown in detail. Although the drawings represent some possible approaches, the drawings are not necessarily to scale and certain features may be exaggerated, removed or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description. Those having ordinary skill in the art will recognize various other permutations of the specifically illustrated design that are understood from the disclosure and all such permutations are within the scope of the present invention.

FIGS. 1A-1O and FIGS. 2A-2C illustrate an exemplary sequential type of patient specific dental surgical guide and dental restoration set with at least one appliance having at least one open-face connector, explaining how the appliance and restoration/transfer jig set may be used in a dental implant surgery and provisionalization procedure. This example is a dentition extraction case that requires bone reduction, but the appliance set can be used in different types of implant surgeries and restoring procedures. It should be noted that, though this example shows a restoring process for a fixed restoration which may be suitable for a case with more implant sites, only two implant sites are shown for simplicity.

The dental appliance set includes multiple pieces and it may include at least one of the following: a fixation site drill guide 101, a bone reduction jig 113A, a surgical drill guide 113B, a transfer jig 113C, a dental restoration 113D, a restoration base 113E, and timing jig 113F and a surgery may be done using any combination of the appliances. The appliance set parts can be digitally designed based on a patient's preoperative master data set which includes at least one of surface scan and/or tomography scan data of the of the patient's oral structure, surface scan and/or tomography scan data of the patient's existing dental restoration, surface scan and/or tomography scan data of the patient's scan appliance, the digital surgical plan created based on the patient's scan data. It may also include scan data of a bite registration and/or a digitized dental restoration design. The 3D designs of the dental appliance parts are stored in a CAM compatible file format (such as .STL and .CAD) in the preoperative master data set keeping the design coordinates of the appliances relative to the coordinates of other preoperative scan and design data, and can be manufactured at least partially by rapid prototyping, CNC milling or any other CAM method. They are made of any medically and physically suitable materials such as but not limited to Resin, PMMA, Zirconium, Titanium, and other dental materials (metal alloy, composite, etc.). It should be noted that the dental appliances 101, 113A-F in this disclosure can be for maxillary or mandibular, and regardless of whichever jaw a particular dental appliance 101, 113A-F is for, the surfaces of the dental appliance 101, 113A-F are defined as follows: (1) The inner surface means the surface configured to be placed adjacent to an oral surface, (2) the outer surface means the surface opposite to the inner surface, (3) the top surface is the outer surface opposite to the inner surface configured to be placed adjacent to the ridge, reduced ridge, incisal or occlusal surface of an oral structure (If a dental appliance 101, 113A-F is for a mandibular, the top surface of the appliance will be positioned above the ridge, reduced ridge, incisal or occlusal surface of the oral structure when it is in place in the mouth. If a dental appliance 101, 113A-F is for a maxillary, the top surface of the dental appliance 101, 113A-F will be seen positioned below the ridge, reduced ridge, incisal or occlusal of the oral structure.).

Figure 1B:
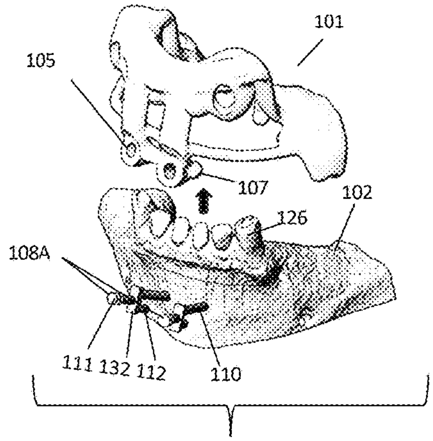
FIG. 1B is a perspective view of a fixation element with a locking bolt.

FIG. 1A is a perspective view of a fixation site drill guide 101 placed on an oral structure 102 and a drill bit 103 aligned to a fixation site. Although FIG. 1A-B illustrates the fixation site drill guide 101 positioned on a patient's remaining teeth 126 and oral structure 102 (lower jawbone), it may be designed to fit any one or multiple other natural or artificial oral structures 102 such as a patient's gum tissue, existing dental implant, crown, bridge and jawbone as shown in FIG. 15*c*. The fixation site drill guide 101 may be designed after an existing denture or a bite registration, both of which contain information that helps position the fixation site drill guide 101 against an opposing jaw. Additionally, the fixation site drill guide 101 may have one or more functions of other dental appliances 113A-F such as a bone reduction jig 113A and a surgical drill guide 113B if an independently designed fixation site drill guide 101 is not required for positioning of the appliance for the case. The fixation site drill guide 101 has a guide frame that stretches along the patient's dental arch covering at least a part of the oral structure 102 surface and has at least one drill guide opening 105 for drilling a planned fixation site positioned on a front lateral surface of the patient's oral structure 102. Optionally, the drill guide opening 105 may have a separately manufactured drill guide sleeve attached (glued or fixated into). If the fixation site drill guide 101 has multiple fixation site drill guide openings 105 for fixation sites, the fixation site osteotomies may be planned generally coplanar so that the fixation elements 108A will be coplanar, considering the insertion axis when attaching the appliance(s) with fixation connectors 104 to multiple fixation elements 108. However, uneven fixation elements 108A can be accommodated by adjusting the design of the fixation connectors 104. The fixation site drill guide 101 may have structural openings that can be used to see the oral structure 102 and make sure the fixation site drill guide 101 is positioned on the oral structure 102 correctly. One or more appliance protrusions 107 may be provided on the fixation site drill guide 101 to contact the oral structure 102 properly. One or fixation site lateral bars 106 may stretch along the lateral surface of the oral structure 102 to position the fixation site drill guide 101 properly. After positioning the fixation site drill guide 101, at least one fixation site hole can be drilled using a suitable size drill bit 103. Optionally, a top or bottom surface of the lateral support bar 106 can be used to mark for a planned bone reduction as shown in FIG. 1B, wherein a dental professional marks the oral structure 102 along the location of the lateral support bar. Then the fixation site drill guide 101 can be removed from the oral structure 102 and at least one fixation element 108A can be partially inserted into the fixation hole. FIG. 1B is a perspective view of the fixation element 108A with the locking bolt 112. Although conventional fixation elements 108 can be used, using a fixation element 108A with a locking bolt 112 allows the users to position various dental appliances 101, 113A-F on the oral structure 102, lock the dental appliances 101, 113A-F to the oral structure 102 if desired, and unlock them for removal without removing the fixation element 108A from the oral structure 102. The fixation element 108A has a fixation element midsection 132, fixation stem 110 extending out of the fixation element midsection 132 and the locking bolt 112 also extending out of the fixation element midsection 132 in the same direction as the fixation stem 110. Though the exemplary fixation element 108A has a cylindrical locking bolt 112, the locking bolt 112 may take a different geometric shape. The fixation element 108A may also have a fixation element distal end 111 extending out from the front body for handling. If the fixation element 108A is used, it may be partially inserted into the oral structure 102 to leave some room (a little more than the thickness of the subsequent dental appliance 101, 113A-F) for the locking bolt 112 to be turned and pushed into a locked position when the subsequent dental appliances 101, 113A-F are positioned on the oral structure 102. As will be detailed further herein, the fixation element 108A may take on different shapes and may use non-integral elements to engage with the fixation connector 105 and/or lock the dental appliances 101, 113A-F into place.

Figure 1C:
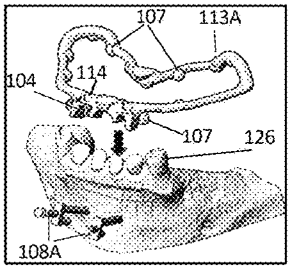
FIG. 1C is an exploded perspective view of a bone reduction jig and the oral structure before teeth extraction.

FIG. 1C is an exploded perspective view of a bone reduction jig 113A and the oral structure 102 before extraction of the teeth 126. The bone reduction jig 113A has a surface that aligns with the planned bone reduction level. The bone reduction jig 113A can be used to finely adjust the alveolar ridge of the jawbone 102. The bone reduction jig 113A may have one or more appliance protrusions 107 abutting the oral structure 102 for positioning, similar to the fixation site drill guide 101. As shown in FIG. 1C, the bone reduction jig 113A may be positioned on the oral structure 102 before the remaining teeth 126 are extracted. Positioning the bone reduction jig 113A on the oral structure is accomplished primarily by attaching the one or more fixation connectors 104 to the one or more fixation element 108A. The appliance protrusions 107 may align the bone reduction jig 113A with the bone reduction level. In the alternative, it may be easier to position the bone reduction jig 113A after extracting remaining teeth 126 depending on the shape of oral structure 102. If the planned bone reduction level is marked by the fixation site drill guide 101 as shown in FIGS. 1B and 1C, the bone can be roughly reduced before placing the bone reduction jig 113A on the oral structure 102 for completing bone reduction.

Figure 1D:
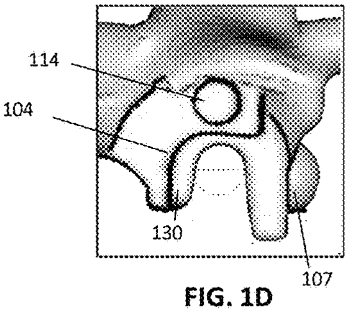
FIG. 1D is a front elevational view of a section of the bone reduction jig.

FIG. 1D is a front elevational view of a section of a bone reduction jig 113A focusing on a single exemplary fixation connector 104. An inner wall of the fixation connector 104 is configured to receive a portion of the fixation element 108A. The fixation connector 104 may have a negative surface that mirrors a surface of the fixation element 108A. The fixation connector 104 may have multiple contact points configured to fit a surface of the fixation element 108A. If the fixation element 108A rotates to engage the fixation connector 104, an inward protrusion 130 of the fixation connector 104 may have a half circle shape as illustrated in FIG. 1D. A width of the opening at a position where the fixation element 108A is fully received may correspond with a diameter of the fixation stem 110. The width of the entry into the fixation connector 104 may taper wider to ease entry of the fixation element 108A, as illustrated in FIG. 1D. The fixation connector 104 may have one or more of the following: (1) a bolt guide 115, (2) a bolt receptor 114, (3) an appliance protrusion 107 that abuts the oral structure 102, and (4) outward tapering extensions to help align to the fixation element 108A, creating an upside-down U- or J-shaped opening as illustrated in FIG. 1D.

Figure 1E:
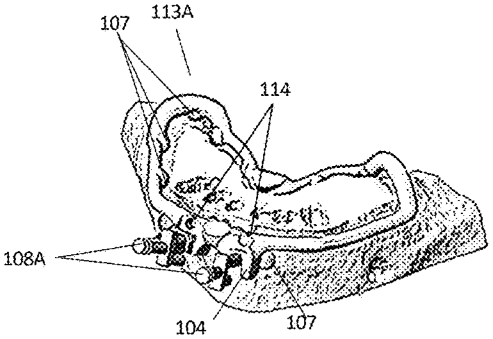
FIG. 1E is a perspective view of a bone reduction jig with open-face connectors placed on the roughly adjusted lower jawbone in a disengaged position.

FIG. 1E is a perspective view of the bone reduction jig 113A with fixation connectors 104 placed on the roughly adjusted lower jawbone in a disengaged position. FIG. 1E illustrates one way that the bone reduction jig 113A can be positioned on the oral structure 102. The bone reduction jig 113A has at least one fixation connector 104 that has an opening corresponding with the fixation element 108A. The fixation stem 110 is illustrated within the fixation connector 104 in an unlocked position. In the unlocked position, the bone reduction jig 113A can be lifted from the oral structure 102 easily.

Figure 1F:
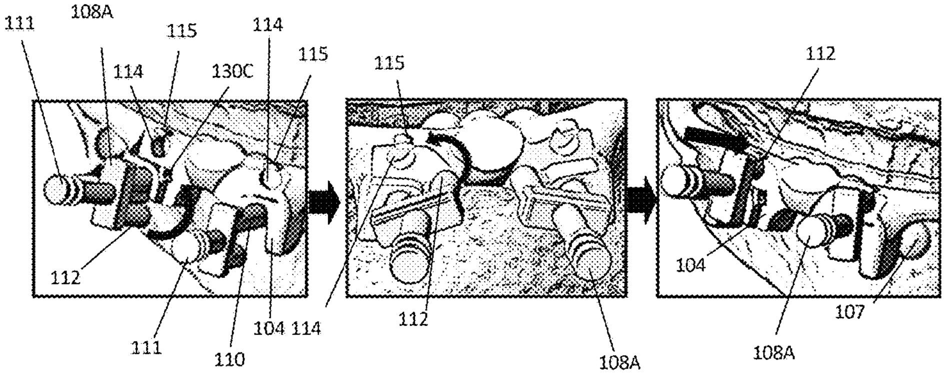
FIG. 1F is a series of perspective views illustrating two fixation elements rotating from a disengaged position to an engaged position.

FIG. 1F is a series of perspective views illustrating two fixation elements 108A rotating from a disengaged position to an engaged position. As shown in FIG. 1F, after the bone reduction jig 113A is placed on the oral structure 102 such that the fixation connectors 104 are placed on the fixation elements 108A, the fixation elements 108A may be rotated to align the locking bolt 112 with the bolt receptor 114. The fixation element 108A may be pushed, urging the locking bolt 112 into the bolt receptor 114 to lock the bone reduction jig 113A in place. As shown in the middle picture of FIG. 1F, the locking bolt 112 may be snapped onto a snap fit protrusion 130C to lock the bone reduction jig 113A into position.

Figure 1G:
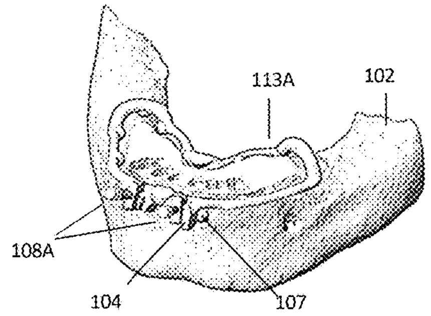
FIG. 1G is a perspective view of the bone reduction jig locked to the oral structure by the fixation elements with locking bolts in engaged positions.

FIG. 1G is a perspective view of the bone reduction jig 113A locked to the oral structure 102 by the fixation elements 108A with locking bolts 112 in engaged positions. Once the bone reduction jig 113A is in a locked position, the alveolar ridge of the oral structure 102 is finely adjusted to the planned bone reduction level using the bone reduction jig 113A. Then, by reversing the sequence shown in FIG. 1F, the fixation element 108A can be returned to the unlocked position, and the bone reduction jig 113A can be removed from the oral structure 102 without removing the fixation element 108A. It should be noted that the locking function may be utilized for some dental appliances 101, 113A-F and not others. If a dental appliance 101, 113A-F does not have to be fixated to the oral structure 102, it can simply rest on the fixation element 108A. Additionally, if the fixation site drill guide 101 has the support bar 106 that provides a bone reduction level marking, bone reduction may not require an independent bone reduction jig 113A.

Figure 1H:
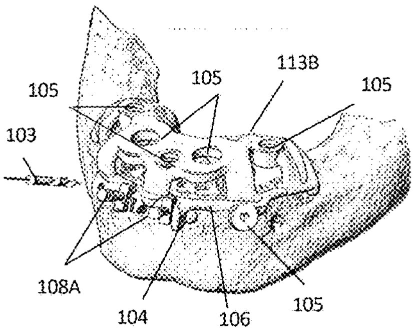
FIG. 1H is a perspective view of a surgical drill guide locked to the oral structure by the fixation elements with locking bolts in engaged positions.

FIG. 1H is a perspective view of a surgical drill guide 113B locked to the oral structure 102 by the fixation elements 108A with locking bolts 112 in engaged positions. The surgical drill guide 113B has at least one implant osteotomy drill guide opening 105 for an implant osteotomy, and at least one fixation connector 104. Optionally, the surgical drill guide 113B may also have one or more extra drill guide openings 105 to fixate the appliance to the oral structure 102 and one or more vertically arranged drill guide openings for creating positioning holes 128 in the oral structure for positioning post(s) 125. One or more of the drill guide openings 105 may have separately manufactured drill guide sleeves 401 (not shown) attached to them. Drill guide sleeves 401 may be constructed to be more adept at incidental contact with the drill bit 103 than the drill guide opening 105, as well as protecting either the drill bit 103 or the drill guide opening 105. Additionally, the surgical drill guide 113B may have one or more appliance protrusions 107 that abut the oral structure 102 for precise placement of the surgical drill guide 113B.

Figure 1I:
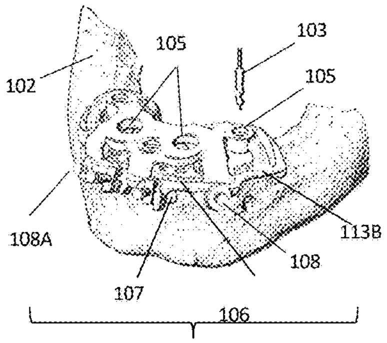
FIG. 1I is a perspective view of the surgical drill guide of FIG. 1H locked to the oral structure by the fixation elements of FIG. 1H and additional fixation elements.

FIG. 1I is a perspective view of the surgical drill guide 113B of FIG. 1H locked to the oral structure by the fixation elements of FIG. 1H and additional fixation elements. Since the fixation elements 108A with locking bolts 112 are still inserted into the oral structure 102, it is easy to position the surgical drill guide 113B on the oral structure 102 using the fixation connectors 104. After the surgical drill guide 113B is positioned and locked to the fixation elements 108A, an additional fixation site (or sites) can be drilled through the drill guide opening 105, if any, as shown in FIG. 1H, and a fixation element 108 can be inserted as shown in FIG. 1I. These fixation elements 108 inserted through a cylindrical drill guide opening 105 must be removed from the oral structure 102 before the surgical drill guide 113B can be removed. At least one osteotomy is drilled through a vertical drill guide opening 105, and, if needed, a positioning hole 128 can be created by drilling through the horizontal drill guide opening 105. Dental implants may be installed through the vertical drill guide openings 105 before removing the surgical guide 113B, which would be more typical with a fully guided system. After the surgical guide 113B is unlocked and removed from the oral structure 102 without removing the fixation element 108A from the oral structure 102, a dental implant abutment or other implant part can be attached to each installed implant.

Figure 1J:
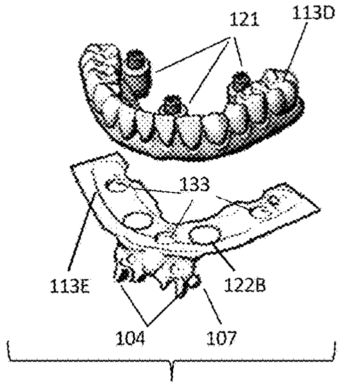
FIG. 1J is a top exploded perspective view of a dental restoration/transfer jig and restoration base assembly.
Figure 1K:
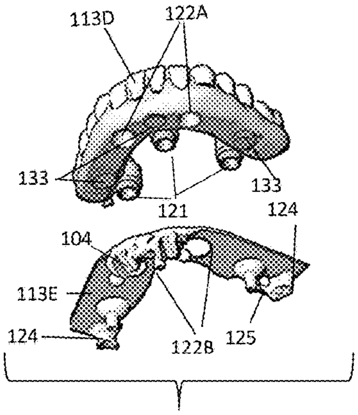
FIG. 1K is a bottom exploded perspective view of the dental restoration/transfer jig and restoration base assembly of FIG. 1J.

FIG. 1J is a top exploded perspective view of a dental restoration 113D and restoration base 113E. FIG. 1K is a bottom exploded perspective view of the combination dental restoration 113D and restoration base 113E of FIG. 1J. If immediate loading is planned, a dental restoration 113D (in this example, temporary) can be positioned on the oral structure 112 using the fixation element 108A attached to the oral structure 102 as a landmark. The dental restoration 113D can be made of PMMA, composite resins or any other suitable dental materials, as known to those having ordinary skill in the art. While a transfer jig 113C is used for physical or digital transferring of position index of installed implants, a dental restoration 113D can be constructed with this functionality, obviating the need for the transfer jig 113C. In this exemplary procedure, a positional index of the installed implants is to be taken to create a physical post-operative master implant model 210. The temporary dental restoration 113D has a separately manufactured restoration base 113E. The restoration base 113E may be attached by an adhesive material, magnetic strips, or other means devisable or known to those having ordinary skill in the art at the time of delivery. The temporary dental restoration 113D and the restoration base 113E may be detachably attachable to each other. As illustrated, each dental appliance 113D-E may have one or more positioning elements 133 that help position the dental restoration 113D on the restoration base 113E. It should be noted that the positioning connector elements 133 may also have a snapping or other mechanical mechanism, utilize magnets, or other temporary attachment mechanisms.

The dental restoration 113D may have a receptor hole 122A for each planned implant site to be positioned over the planned implant site so that an implant part, such as an implant sleeve 123, can be inserted into the receptor hole 122*a* when engaging the dental restoration 113D to the oral structure 102. The receptor hole 122A should be larger than the diameter of the implant sleeve 123 to provide tolerance for deviation in placement. The dental restoration 113D may also have a model connector 204 connectable to a model base 201 if the dental restoration 119D is used for the physical transfer of the positioning index of installed implants. The restoration connector 121 can be manufactured as a part of the dental restoration 113D. The restoration connector 121 provides a mechanical means of connection, which may include a threaded connection.

The restoration base 113E has a through-hole 122B aligned with each receptor hole 122A on the dental restoration 113D and with the oral structure 102. The restoration base 113E may have one or more of the following: (1) a fixation connector 104 that corresponds with the fixation elements 108A attached to the oral structure 102, (2) a positioning post 125, (3) an oral structure rests 124, and (4) a top contour to match the bottom of the dental restoration 113D. The dental restoration 113D may have one or more restoration connectors 121 connectable to the model base 201. Additionally, the restoration base 113E may have one or more guide holes that aligns with the previously drilled extra fixation holes.

Figure 1L:
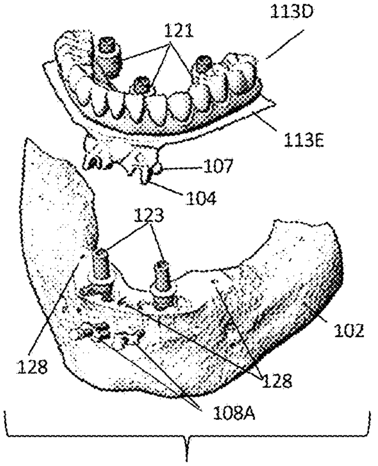
FIG. 1L is a perspective view of the dental restoration/transfer jig and the restoration base assembly of FIGS. 1J-1K above the oral structure with the fixation elements and implant components.

FIG. 1L is a perspective view of the dental restoration 113D and the restoration base 113E of FIGS. 1J-1K above the oral structure 102 with the fixation elements 108A and implant sleeve 123. The dental restoration 113D and the restoration base 113E are temporarily attached, using a suitable biocompatible means. In a preferred embodiment, the biocompatible means is a suitable adhesive. The implant sleeves 123 are attached to the implant abutments on the installed implants by dental screws. Positioning holes 128 have been formed in the oral structure.

The implant sleeves 123 and other implant parts relate to known structure in the art of dental restoration for establishing connections to the dental appliances 101, 113A-F in the lingual area. These elements may include commercially available parts, including copings, multi-unit abutments, implant analogs, scan bodies, reverse scan bodies, impression copings, locator abutments, and implant bars. As described herein, the implant sleeves 123 and related structure may be used to connect dental appliances 101, 113A-F to the oral structure 102 and/or the model base 201. However, the use of these implant parts will not supplant the use of the fixation element 108A and fixation connector 104.

Figure 1M:
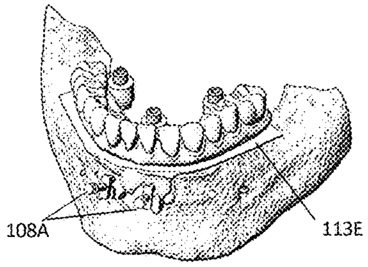
FIG. 1M is a perspective view of the dental restoration and the restoration base of FIGS. 1J-1L engaged on the oral structure by the fixation elements.
Figure 1N:
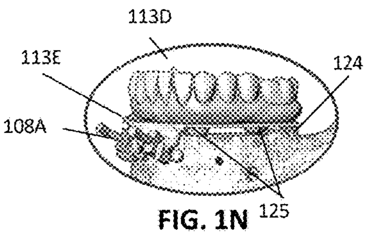
FIG. 1N is a side perspective view of the illustration in FIG. 1M with the dental restoration/transfer jig and the restoration base engaged on the oral structure by the fixation elements.

FIG. 1M is a perspective view of the dental restoration 113D and the restoration base 113E of FIGS. 1J-1L engaged on the oral structure 102 by the fixation elements 108A. FIG. 1N is a side perspective view of the illustration in FIG. 1M with the dental restoration 113D and the restoration base 113E engaged on the oral structure 102 by the fixation elements 108A. As illustrated, the combined dental restoration 113D and restoration base 113E can be attached and locked to the fixation elements 108A like other dental appliances 101, 113A-F. If the restoration base 113E has one or more positioning posts 125 and/or oral structure rests 124, the positioning posts 125 can be aligned and inserted into the positioning holes 128 created in the oral structure 102, and the structure rests 124 can rest on the oral structure 102. The restoration base 113E may have both positioning post 128 and fixation connector 104, but the restoration base 113E may be positioned on the oral structure 102 accurately with just one of those features.

Once the dental restoration 113D and restoration base 113E are secured on the oral structure 102, the implant sleeve 123 can be glued to the dental restoration 113D using a dental material such as acrylic resin or other adhesive known to those having skill in the art. Then, the implant sleeve 123 can be unscrewed and detached from the implant abutments in the oral structure 102 and the dental restoration 113D and the restoration base 113E can be removed from the oral structure 102 along with the attached implant sleeve 123.

Figure 1O:
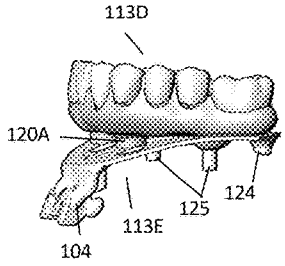
FIG. 1O is a perspective side view of the dental restoration with a restoration base partially peeled away.

FIG. 1O is a perspective side view of the dental restoration 113D with a restoration base 113E partially peeled away. Just like other dental appliance parts, the restoration base 113E can be made of any suitable dental materials but may be made of a resin material with some elasticity with a thin area of the restoration base 113E bendable as shown in FIG. 1O. The restoration base 113E can be peeled off from the dental restoration 113D before the final seating in the mouth. Since the dental restoration 113D does not have connectors on the facial side where aesthetics is important, it is easier to complete the dental restoration 113D for seating after the positional index of installed implants is transferred to a master implant model 210 and/or recorded as a digital scan file by scanning the dental restoration 113D with implant analogs 207 or scan bodies attached to the implant sleeves 123 picked up from the installed implants. The advantages of the peelable dental restoration base 113E are as follows: (a) The peelable restoration base 113E can be very thin and there is minimal availability of space between the dental restoration 113D and oral structure 102, or within the mouth more generally, to have a separate dental appliance; and (b) since the restoration base 113E is glued to the dental restoration 113D, the dental restoration 113D will not move around on the restoration base 113E. It should be noted that this peelable type of restoration base 113E combined with a dental restoration 113D can be made as a super structure of a stackable drill guide set. In that case, the restoration base 113E may have connector legs connectable to the dental restoration 113D of the stackable guide set. The restoration base 113E (peelable or detachably attachable) with one or more fixation connectors 104 can be attached to different types of transfer jigs 113C which do not include any teeth design. For example, if a transfer jig 113C needs to be made with very hard material, a simple metal plate (or plate made of other hard material) with holes at planned implant sites can be held by the restoration base 113E with the fixation connector(s) 104) with an adhesive material or physical retention created by a shallow and tight lateral wall on the top surface of the restoration base 113E, encasing the edge around the transfer jig 113C. The restoration base 113E may also have one or more restoration connectors corresponding with the threaded model connector 205 on a model base 201 if the master implant model 210 is to be created.

Figure 2A:
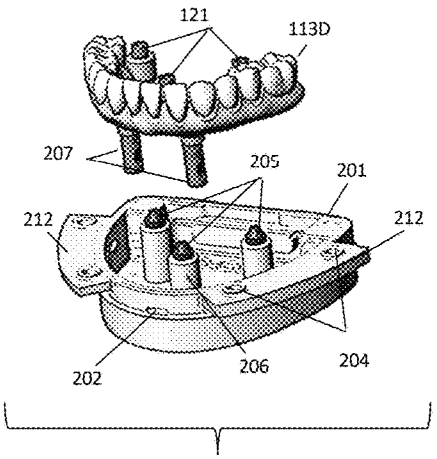
FIG. 2A is an exploded perspective view of the dental restoration above a model base.
Figure 2B:
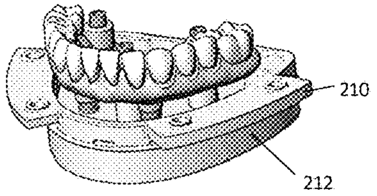
FIG. 2B is a perspective view of the dental restoration attached to the model base.

FIG. 2A is an exploded perspective view of the dental restoration 113D above a model base. FIG. 2B is a perspective view of the dental restoration 113D attached to the model base 201. If the dental restoration 113D has the functionality of the transfer jig 113C, the positional index of installed implant(s) can be transferred to a model base 201 to create a master implant model 210 by attaching an implant analog 207 to each implant sleeve 123 glued to the dental restoration 113D and positioning on a model base 201. The model base 201 has a hollowed tub section at least around the area that the implant analog(s) 207 are expected to be placed. The model base 201 has one of a bottom wall and a removable bottom (The exemplary model base 201 has a bottom wall). The model base 201 may also have a fill line to be used when pouring a model material into the hollowed area of the model base 201, one or more spill windows 202 that prevent the model stone from overfilling the model base 201, one or more wings 212 which may hold model connector(s) 204 for a different appliance or appliances, and one or more threaded model connectors 205 corresponding with the connectors on the dental restoration 113D and/or a transfer jig 113C.

Figure 2C:
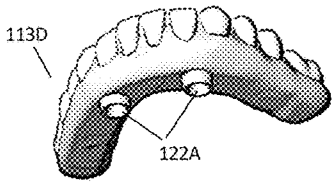
FIG. 2C is a bottom perspective view of the dental restoration of FIGS. 2B-2C after restoration connectors are removed.

The dental restoration 113D has multiple screwable connectors 121, and they can be securely connected to the connector elements 205 on the model base 201 by screws or other fasteners. In this case, the model base 201 has a connector stem 206 to hold implant analogs 207 available on the market to be inserted from the bottom of the model base 201 in the planned locations and to work as threaded model connectors 205 that are connectable to the restoration connectors 121 on the dental restoration 113D. The restoration connectors 121 on this exemplary restoration 113D may include temporary implant components 123 that may be glued to connection holders on the dental restoration 113D. It should be noted that the threaded model connectors 205 on the model base 201 and dental restoration 113D may be any type of mechanical or magnetic connectors known to those having ordinary skill in the art to be usable in this type of application. After the dental restoration 113D is securely to the model base 201, a model material can be poured into the model base 201 to make a master implant model 210 as illustrated in FIG. 2B. Model material may expand as it hardens. Expansion is not desirable if the model base 201 is pre-articulated to the patient's opposing model. However, since this exemplary assembly uses restoration connectors 121 to secure the dental restoration 113D to the model base 201, the height of the implant analogs 207 buried in the model material relative to the model base 201 maintain the planned spatial orientation. If a less reliable connector is used to position the dental restoration 113D on the model base 201, a rubber band can be hooked and twisted around the wings 212 over the dental restoration 113D to restrain movement as the model material expands. As shown in FIG. 2C, after being removed from the model base 201, the restoration connectors 121 can be removed from dental restoration 113D, and it can be touched up to be seated in the patient's mouth.

Although post-operative dental appliances and restorations, such as a verification jig, a try-in, temporary or final dental restoration 113D, can be created on the master implant model 210 in the traditional way. In order to digitally design these appliances and restorations, a digital postoperative master implant model 210 needs to be created, and there are mainly four ways to do so: [Method 1] Scan the master implant model 210 to digitize the master implant model 210, [Method 2] After picking up a positional index of the installed implant(s), attach reverse scan bodies (i.e. Straumann RevEX) to the implant sleeve 123 glued to the dental restoration 113D or other transfer appliances that operate with functionality of the transfer jig 113C (i.e. surgical guide 113B shown in FIGS. 16A-B and 17A-B) in and extra-orally scan the dental appliance 113A-F. [Method 3] Attach proper scan bodies to the installed implants and scan (or taking pictures of) the patient's mouth. [Method 4] Obtain a digital record of 3D coordinates of a constant fiducial marker or markers oriented to the patient's preoperative digital dental model before making any significant changes on the patient's oral structure 102 (extraction of remaining teeth 126 or bone reduction if it is a fully edentulous case) and scan (or taking a picture of) the patient's mouth with scan bodies attached to installed implants along with the same constant fiducial marker or markers. Each method will be explained in detail in the following paragraphs. It should be noted that, for scanning, different types of scanners and scanning techniques known to those having ordinary skill in the art can be used such as intraoral scanning and extraoral scanning with a time-of-flight (ToF) scanner, a stereoscopic scanner, a light field moment scanner, a fixed structured light scanner, a programmable structured light scanner (DLP), 3D or 4D ultrasound scanner, digital camera scanner, light-emitting diode (LED) scanner and laser scanner, etc. without departing from the scope of the present disclosure. It should be noted that, in this disclosure, the photogrammetry techniques and its camera equipment (used on the patient's mouth or on the master implant model 210) may be also included in the group of 'scanning' techniques, and a 'scanner'.

[Method 1] If the master implant model 210 is scanned and digitized, the scan data can be aligned to the preoperative digital models such as preoperative digital dental model before teeth extraction, the planned restoration digital design, and the digital bite registration to utilize preoperative occlusion information by aligning the coordinates of the model base 201 in the scan data of the master implant model 210 to the corresponding coordinates of the digital design of the model base 201 stored and oriented to the digital preoperative model(s) in the preoperative master data file which also include other appliance designs whose coordinates are oriented to one another and to the preoperative digital model(s). To adjust any minor positional deviation of the design of the model base 201 which may occur during positioning of a fixation site drill guide 101 and drilling of a fixation site (or sites), an additional scan (or additional pictures) of the oral structure 102 can be taken with a fixation site drill guide 101 fixated with a fixation element 108A, a bone reduction jig 113A fixated with a fixation element 108A, or just a fixation element 108A. If a fixation site drill guide 101 is in place while scanning the oral structure 102, the fixation site drill guide 101 should have good visibility of the remaining teeth 126 and/or other part of oral structure 102 when it is positioned in the oral structure 102, as with the configuration of the fixation site drill guide 101 in FIGS. 4 and 12 which has appliance protrusions 107 and minimized obstructions to the remaining teeth 126, oral structure 102 and/or gum tissue and air space around the oral structure 102. The adjustment of positional deviation (if any) for this method can be done by aligning the coordinates of remaining teeth 126 (and/or other oral structure parts) on the new scan data to the corresponding 3D coordinates of the teeth 126 (and/or other parts of oral structure 102) in the preoperative digital dental model in the master data file. By doing so, the 3D coordinates of the fixation site drill guide 101 in the extra scan data will be correctly oriented to the preoperative digital dental model, and the coordinates of the design of fixation site drill guide 101 in the master data file can be aligned to the corrected coordinates of the fixation site drill guide 101 along with the coordinates of other designs of dental appliances 113A-F, including the coordinates of the design of the model base 201. Similarly, if a bone reduction jig 113A is placed in the patient's mouth while scanning the oral structure 102, the extra scan data can be oriented to the preoperative digital model by aligning the patient's oral structure 102 and/or teeth 126 in the scan data to the corresponding coordinates on the digital preoperative dental model, and by aligning the coordinates of the digital design of the bone reduction jig 113A to the corresponding coordinates in the extra scan, the coordinates of all dental appliances 113A-F designs including the design of the model base 201 can be correctly oriented to the preoperative dental model. Then the coordinates of the scanned master implant model 210 can be aligned to the preoperative digital model using the coordinates of the model base 201 portion in the scan data. If the patient's mouth is scanned (or taken pictures of) with one or more fixation elements 108A (or 108B or 108C) without any dental appliances 113A-F attached to them before making any significant adjustment to the oral structure 102, the following can be done: After the scan data is aligned to the preoperative digital dental model, using the coordinates of the oral structure 102 in the extra scan data that commonly exist on the digital preoperative dental model in the master data file, the coordinates of planned fixation element 108A locations can be aligned to the corrected positions along with the coordinates of the design of digital dental model. If the fixation elements 108A are to be used as fiducial markers, they may have distinctive geometric shapes to work as scan markers or have parts like the fiducial markers 2501 (shown in FIG. 25B) attached. It can also be replaced with a scan body or bodies during the scan, and in that case, the 3D design and position(s) of the scan body/marker should be also stored in the master data file. Alternatively (or additionally), if one or more vertical or horizontal holes are drilled, one or more scan bodies can be inserted into the drilled holes and included in the scan taken before making significant changes to the oral structure 102. The scans can be used for adjusting any positional deviation.

[Method 2] Similarly, if a dental restoration 113D is used as a transfer jig 127 after occlusion, a brand new digital dental model may be created without aligning the data to preoperative digital dental model since it already has the occlusion information. However, if desired, the digital positional index taken with this method can be aligned to the preoperative digital dental model in the master data file that includes the 3D coordinates of the design of dental restoration 113D or other transfer jig appliance 113C by aligning the coordinates of unadjusted portion of the dental restoration 113D in the scan with positional index of installed implants to the corresponding coordinates of the design of dental restoration 113D. To adjust any positional deviation of the design of appliances and fixation sites, the same methods can be used as explained above. Since the digital positional index of installed implant sleeve 123 is recorded with the dental restoration 113D, after the appliance designs and fixation sites in the master dental file are reoriented to the digital preoperative dental model as previously explained, the 3D coordinates of unadjusted portion of the dental restoration 113D in the digital record of positional index of installed implants can be aligned to the corresponding coordinates of the design of the dental restoration 113D that are now in correct position. [Method 3] If the positional index was taken with scan bodies attached to the installed implants after the significant changes are made on the oral structure 102, the digital positional index cannot be aligned to preoperative digital dental model without any constant fiducial marker that exist both in the preoperative digital dental model and the postoperative scan with the positional index of installed implant and the patient's preoperative occlusion cannot be utilized.

[Method 4] This method is also about taking a digital positional index of the installed implants by scanning (or taking pictures of) patient's mouth with scan bodies attached to the installed implants like the [Method 3]. However, since this method will use one or more fiducial markers for aligning the postoperative scan data with positional index of installed implants to the preoperative digital dental model, the preoperative occlusion information can be utilized for making a final restoration. To align the postoperative scan data with positional index to the preoperative digital dental model in the preoperative master data file the following methods can be used: (I) Keep the fixation elements 108 in the oral structure 102 and take the digital positional index of installed implant(s) with scan bodies and fixation elements 108. Even though the scan data with positional index can be aligned to the digital preoperative dental model by aligning the 3D coordinates of the fixation elements 108 in the scan data with positional index to the coordinates of planned positions of fixation pins/screws, alignment will be easier if an extra scan (or pictures) of the patient's mouth before making any significant changes (such as extraction of remaining teeth) with the fixation elements 108 in place preferably with scan markers (such as the fiducial markers 2501) is taken. Then, the extra scan can be aligned to the digital preoperative model in the master data file using unchanged parts of the oral structure 102 and/or teeth 126 as common fiducial markers, and the post operative scan with the positional index of installed implant can be aligned to the digital preoperative model by aligning the 3D coordinates of the fixation elements 108 in the postoperative scan to the corresponding coordinates of the fixation elements 108 in the extra scan already aligned to the preoperative digital model. (II) Keep the fixation elements 108 in the patient's mouth, attach a bone reduction jig 113A, a transfer jig 113C or other dental appliance 113B, D-F that has an open view of the implant sites, and scan the patient's mouth with scan bodies attached to the installed implants. As explained with the [Method 1] and [Method 2] the postoperative scan with positional index can be aligned to the digital dental model by aligning the coordinates of the dental appliance 101, 113A-F scanned with the positional index to the corresponding coordinates of the same dental appliance 101, 113A-F alone. To adjust any positional deviation of the dental appliance 101, 113A-F an extra scan can be taken before making any significant changes to the oral structure 102. Since the transfer jig 113C cannot be positioned on the oral structure 102 before adjustment of the oral structure 102, a fixation site drill guide 101 or a bone reduction jig 113A can be used to take the extra scan (or pictures) and adjust the coordinates of the fixation elements 108 along with all the designed appliances as previously explained. Then, after the postoperative scan with positional index of the installed implant sleeve 123 is taken with an appliance, it can be aligned to the preoperative digital dental model by using the fixation elements 108 or attached and/or the dental appliance 101, 113A-F included in the postoperative scan as a fiducial marker or markers. If the dental appliance 101, 113A-F is the same as the one that was used for the extra scan taken before the alteration of oral structure 102 (i.e. bone reduction jig 113A), the 3D coordinates of the dental appliance 101, 113A-F can be just aligned to the corresponding of the dental appliance 101, 113A-F in the extra scan data aligned to the digital preoperative dental model. If the dental appliance 101, 113A-F is different from the one in the extra scan, the coordinates of the dental appliance 101, 113A-F can be aligned to the corresponding coordinates of the digital design of the same dental appliance 101, 113A-F that was reoriented to the digital model as previously explained. (III) Drill one or more positioning holes 128 or one or more extra horizontal holes with a fixation site drill guide 101 for inserting positioning pins 1501 that can be used as scan bodies or scan bodies. Take an extra scan of the mouth before making significant changes to the oral structure 102 with the positioning pins 1501 or scan bodies in place. One or more fixation elements 108 inserted into the fixation holes on the oral structure 102 can be included in the scan data also to be used as additional fiducial markers as well. Then, take a postoperative scan (or pictures) with a positional index of installed implant can be taken with those fiducial markers.

The digital positional index of installed implants can be aligned to the digital preoperative dental model by aligning the extra scan first to the digital preoperative dental model, and then, aligning the postoperative scan with the positional index to the extra scan data already aligned to the preoperative dental model, using the common fiducial markers that exist both in the extra scan and the postoperative scan.

Once the digital implant model is made, new postoperative scan data such as healed gum tissue scan taken with scan bodies can be aligned to the digital model using the positions of the installed implant in the digital data as fiducial markers. Moreover, even if the master implant model 210 was not made with a transfer jig 113C, a master implant model 210 can be manufactured from the digital dental model. Various types of postoperative dental appliances 101, 113A-F or restorations can be created based on the digital implant model and/or physical implant model 210 including a verification jig, a try-in appliance, try-in dental restoration, implant bar, and dental restoration 113D. Some appliances and restorations may be designed partially on the digital implant model to be assembled with implant parts on the master implant model 210. If the appliance or restoration is designed fully on the digital implant model, the master implant model 210 can be used to verify the fit.

Figure 3A:
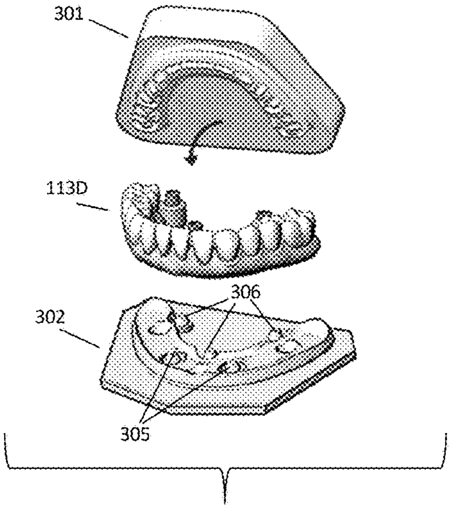
FIG. 3A is an exploded perspective view of a dental restoration above a post-operative gum tissue model and below a bite registration model.
Figure 3B:
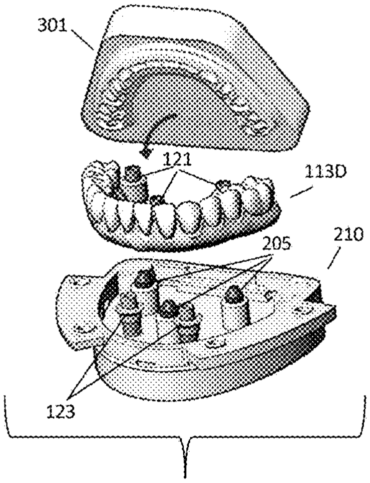
FIG. 3B is a perspective view of the dental restoration above the master implant model and below the bite registration model.
Figure 3C:
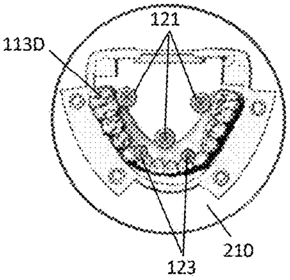
FIG. 3C is a top plan view of the dental restoration placed on the master implant model.

FIG. 3A is an exploded perspective view of a dental restoration 113D above a post-operative gum tissue model 302 and below a bite registration model 301. FIG. 3B is an exploded perspective view of the dental restoration 113D above the master implant model 210 and below the bite registration model 301. FIG. 3C is a top plan view of the dental restoration 113D placed on the master implant model 210. FIGS. 3A-C illustrate how the master implant model 210 can be used to fabricate a dental restoration 113D, especially with substructures made of metal, ceramic or other dental materials. The bite registration model 301 can be digitally or manually created based on the patient's post operative bite against the dental restoration 113D after the surgery. Instead of the bite registration model 301, a regular dental model may be used as an opposing model in this assembly, but, in that case, the model assembly may have to be articulated using a traditional bite registration. The dental restoration 113D can be digitally designed on the digital postoperative implant model created as previously explained according to the positional index of the installed implants and manufactured at least partially by rapid prototyping, CNC milling or any other CAM method. The final (or try-in) dental restoration 113D design can be very similar to the temporary dental restoration 113D, but the receptor holes 122A for implant sleeves 123 or other types of restoration substructures can be made precisely to fit onto the implant sleeves 123 or other types of restoration substructures since the final dental restoration 113D is designed according to the actual install implant positions. The final dental restoration 113D may also have one or more restoration connectors 121, preferably on the lingual side for aesthetic reasons, connectable to the threaded model connectors 205 on the master implant model 210 similar to the temporary dental restoration 113D.

The gum tissue model 302 can be created based on the patient's postoperative gum tissue information. A regular gum tissue model made by conventional method can be used as a part of the model assembly. However, the coordinates of a part of the dental restoration contour design, connector design or other design elements stored in master data file can be incorporated into the postoperative gum tissue model 302 if it is digitally designed as shown in FIG. 3B. The digitally designed gum tissue model 302 can be created generally in following steps: (1) After the patient's gum tissue is healed, obtain the postoperative gum tissue information either by scanning with scan bodies attached to the installed implants or by taking an impression of the gum tissue with impression copings attached to implant abutments or the installed implants and digitizing the impression or poured model. (2) Align the digital gum tissue and implants surface coordinates to the coordinates in the master data set, and (3) Create a digital design of the post operative gum tissue model 302 incorporating some of the design elements of other appliances, (4) Manufacture the gum tissue model 302 by rapid prototyping. The exemplary gum tissue model 302 has a gum tissue surface that represents the patient's post operative gum tissue surface and a replica of the implant abutment 305 representing each installed implant abutment. It may also have one or more of the following features: (a) one or more of gum connectors 306 that replicate the threaded model connectors 205 on the master implant model 210 (these connectors may be threaded), (b) a lateral wall whose inside surface is generally a negative of the lower lateral surface of the final dental restoration 113D so that the final dental restoration 113D can be held inside. It should be noted that there are many design variations to the dental appliances 101, 113A-F and their features, and they will be discussed in the following paragraphs. A bottom surface of the dental restoration 113D can be adjusted to fit to the post operative gum tissue surface according to this gum tissue model 302, and the bite can be adjusted according to the bite registration model 301.

FIG. 3B illustrates the dental restoration 113D above the master implant model 210 with implant sleeves 123 and below a bite registration model 301. After the gum tissue and occlusal surfaces of the dental restoration 113D is adjusted and finished according to the gum tissue model 302 and bite registration model 301, the final implant sleeves 123 can be screwed to implant analogs 207 on the master implant model 210. Then, the restoration connectors 121 on the dental restoration 113D can be attached to the corresponding threaded model connectors 205 on the master implant model 210 and the implant sleeves 123 can now be cemented to the receptor holes 122A on the dental restoration 113D. Since the exemplary dental restoration 113D and the master implant model 210 have connectors 121 and 205 that are threadably attachable, the dental restoration 113D can be precisely positioned and properly oriented independently and collectively to the head of implant analogs 207 representing installed implants on the master implant model 210, the gum tissue model 302 and the bite registration model for assembling, verifying and adjusting. Therefore, the implant sleeves 123 can be precisely attached to the dental restoration 113D one at a time or all together, and, unlike a traditional model system, this model system with threaded model connectors 205 along with bite registration model 302 does not require articulation. It should be noted that the connectors 121 and 205 on the dental restoration 113D and master implant model 210 can be different type of connectors if they can securely connect the dental restoration 113D and master implant model 210. If the dental restoration 113D is manufactured remotely based on postoperative scan and it includes the interface to the implant parts attached to the installed implants, the master implant model 210 can be used to verify the fit prior to the patient's appointment for seating.

FIGS. 4-11D illustrate examples of design variations and usage variations of the fixation connectors 104, fixation elements 108, and related parts.

Figure 4:
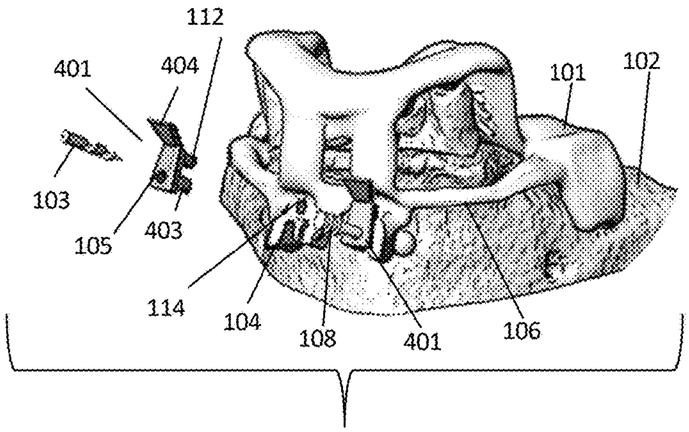
FIG. 4 is a partially exploded perspective view of an exemplary fixation site drill guide placed on the oral structure with drill guide sleeves with locking bolts.

FIG. 4 is a partially exploded perspective view of another exemplary fixation site drill guide 101 placed on the oral structure 102 with a drill guide sleeve 401 having locking bolt 112. The drill guide sleeve 401 engages with fixation connector 104 and provides a guide for drilling oral structure 102 with the drill bit 103. The drill guide sleeve 401 has a locking bolt 112 that extends out from the body to be inserted into the bolt receptor 114 to lock the drill guide sleeve 401 onto the fixation connector 104 similar to locking bolt 112 on the fixation element 108A. A guide sleeve proximate end 403 extends out from the body of the drill guide sleeve 401 to be inserted into the opening of the fixation connector 104. A drill guide opening 105 extends through the guide sleeve proximate end 403 and opens for drilling a fixation hole on the oral structure 102 and accepting a fixation element 108. The drill guide sleeve 401 may also have a guide sleeve distal end 404 that extends out for handling the drill guide sleeve 401.

The design of the exemplary fixation site drill guide 101 in FIG. 4 is very similar to the fixation site drill guide 101 shown in FIG. 1A. A difference is that the fixation site drill guide 101 in FIG. 1A has drill guide openings 105 that form a substantially cylindrical opening whereas the fixation site drill guide 101 of FIG. 4 utilizes fixation connectors 104 as found on other dental appliances 113A-F. When a detachably attachable drill guide sleeve 401, as shown in FIGS. 4-6*c* and FIG. 9, is to be inserted into the opening of the fixation connector 104, the fixation connector 104 must be sized to receive the drill guide sleeve 401.

After fixation site drill guide 101 is positioned on the oral structure 102, the drill guide sleeve 401 can be inserted into the fixation connector 104. The locking mechanism of the locking bolt 112 bolt is comparable to the locking bolt 112 of the fixation element 108A. Once the drill guide sleeve 401 is securely locked to the fixation connector 104, a fixation site hole can be drilled through the drill guide sleeve 401. After the planned fixation hole or holes are created, a fixation element 108 can be inserted into each fixation site through the drill guide opening 105 on the drill guide sleeve 401. When inserting the fixation element 108, it may be useful to leave enough room for the drill guide sleeve 401 to freely slide in and out of the fixation connector 104 without removing the fixation element 108. In any of the embodiments provided herein, it is desirable to insert the fixation elements 108 once and leave the fixation elements 108 stationary until the fixation elements 108 are no longer needed. To unlock the fixation site drill guide 101, pull the drill guide sleeve 401 out of the fixation connector 104. While doing so, the fixation element 108 does not have to be detached from the oral structure 102. Subsequent appliances 113A-F with the fixation connector 104 can be positioned on the oral structure 102 easily without losing the landmark(s). The subsequent appliances 113A-F can be locked to the oral structure 102 by reversing the previously explained unlocking method. The fixation connector 104 may be formed deeper or shallower than illustrated without departing from the scope of the present disclosure. Size or depth of the fixation connector 104 should be coordinated between dental appliances 101, 113A-F and design of the grill guide sleeve 401.

Figure 5A:
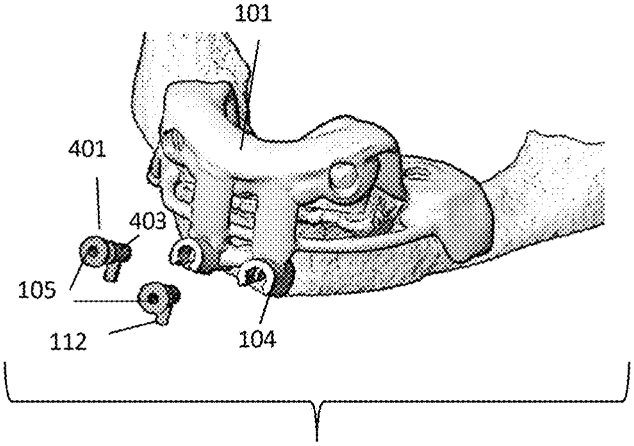
FIG. 5A is a partially exploded perspective view of an exemplary fixation site drill guide placed on the oral structure illustrated with drill guide sleeves having locking bolts.
Figure 5B:
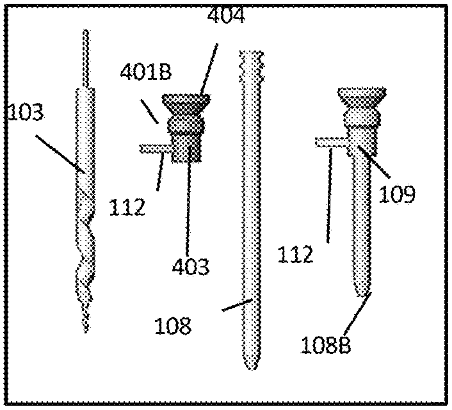
FIG. 5B is a side view of a drill bit, the drill guide sleeve of FIG. 5A, a fixation element and fixation element with a locking bolt.

FIGS. 5A-5J illustrate another detachably attachable drill guide sleeve 401 which has a swing type locking bolt 112. FIG. 5A is a partially exploded perspective view of an exemplary fixation site drill guide 101 placed on the oral structure 102 illustrated with drill guide sleeves 401 having locking bolts 112. FIG. 5B is a side view of a drill bit 103, the drill guide sleeve of FIG. 5A, a basic fixation element 108 and a locking bolt type fixation element 108B. The drill guide sleeve 401 has a guide sleeve proximate end 403, a drill guide opening 105 that passes through a middle portion of the drill guide sleeve 401 and opens to the rear end of the guide sleeve proximate end 403, and a locking bolt 112 extending out of the drill guide sleeve 401 perpendicular to an axis of the drill guide sleeve 401. The drill guide sleeve 401 may be wider at a midsection or at the guide sleeve distal end 404 to limit the depth to which the drill guide sleeve 401 can be pushed into the fixation connector 104.

Figure 5C:
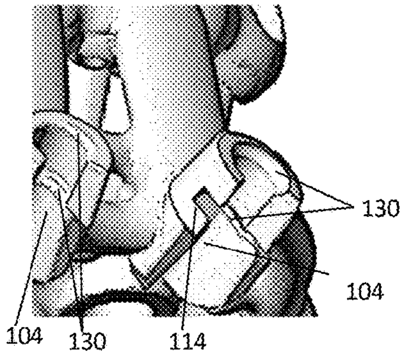
FIG. 5C is a bottom perspective sectional view of an exemplary fixation connector.
Figure 5D:
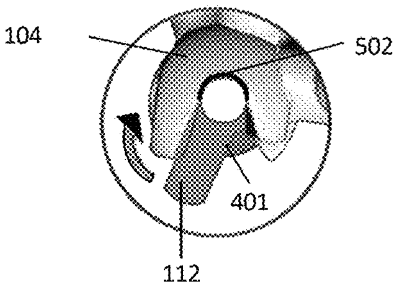
FIG. 5D is a rear elevational sectional view of the fixation connector engaged with the drill guide sleeve having the locking bolt.

FIG. 5C is a bottom perspective sectional view of an exemplary fixation connector 104. FIG. 5D is a rear elevational sectional view of the fixation connector 104 engaged with the drill guide sleeve 401 having the swivel-type locking bolt 112. As shown in FIG. 5C, though the corresponding fixation connector 104 for the sleeve 401 is similar to the fixation connector 104 shown in FIG. 4, the fixation connector 104 in FIG. 5C has a C-shape that pinches in at the ends and a slit-type bolt receptor 114 instead of cup-shaped lock receptor 114 of FIG. 4. The fixation connector 104 in FIG. 5C also has a front extension that protrudes from the facial surface for the fixation site drill guide 101. The slit-type bolt receptor 114 may be formed on a lateral surface of the front extension of the fixation connector 104 and to accept the locking bolt 112 drill guide sleeve 401.

The fixation connector 104 may also have additional features. The fixation connector 104 may have one or more inward protrusions 130 to limit further entry of the drill guide sleeve 401 through contact with a midsection protrusion or wider guide sleeve distal end 404 on the drill guide sleeve 401. FIG. 5D is a rear elevational sectional view of the fixation connector 104 engaged with the drill guide sleeve 401 having the locking bolt 112. As can be seen in this rear view, an extended support wall 502 is configured to cover and support the fixation element 108. As, the extended support wall 502 can be important if the detachably attachable drill guide sleeve 401 is positioned too far from the lateral surface of the oral structure 102 to support the fixation pin 108 as shown in FIG. 5I. The extended support wall 502 covers a portion of the circumference of the fixation pin 108 when inserted and aligns with a portion of the circumference of the drill guide opening 105 of the attachable drill guide sleeve 401. It should be noted that the opening of the open-face connector 104 below the extended support wall 502 may flare out backwardly and downwardly to accommodate the path of insertion of the dental appliance (s) 101, 113A-F.

Figure 5E:
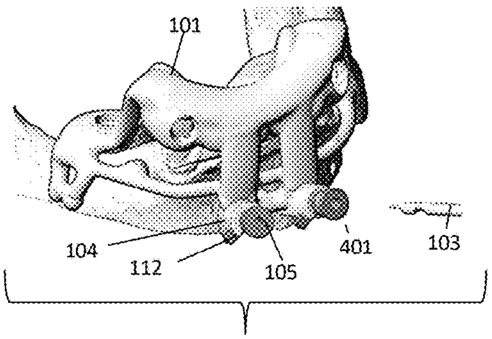
FIG. 5E is a perspective view of the fixation site drill guide on the oral structure with the drill guide sleeves in an engaged position within the fixation connectors.
Figure 5F:
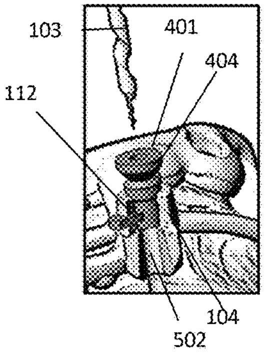
FIG. 5F is a bottom perspective view of the fixation site drill guide mounted on the oral structure with the drill guide sleeves in an engaged position within the fixation connector.

FIG. 5E is a perspective view of the fixation site drill guide 101 on the oral structure 102 with the drill guide sleeves 401 in an engaged position within the fixation connectors 401. FIG. 5F is a sectional bottom perspective view of the fixation site drill guide 101 mounted on the oral structure 102 with the guide sleeves 401 in an engaged position within the fixation connector 104. Additionally, a width of the opening of fixation connector 104, at the end of the C-shape of the fixation connector 104, may be narrower than the outer diameter of the guide sleeve proximate end 403 in the area where the drill guide sleeve 401 is held to cover more than half of surface of the guide sleeve proximate end 403 when assembled. The detachably attachable drill guide sleeve 401 can be detached from the open-face connector 104 by pulling from the fixation connector 104 axially. The opening at the end of the C-shape of the fixation connector 104 needs to be larger than the diameter of the fixation stem of the fixation element 108. In this way, the drill guide sleeve 401 will not fall out of the fixation connector 104 once seated. It should be noted that this type of opening design of the fixation connector 104 can be used similarly in conjunction with other drill guide sleeve 401 or fixation element 108 designs.

Figure 5G:
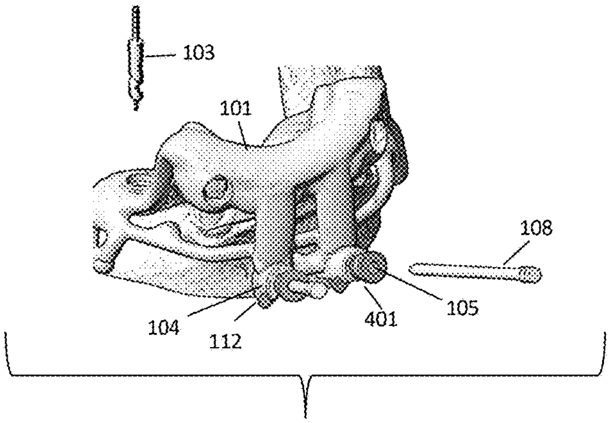
FIG. 5G is a partially exploded perspective view of the fixation site drill guide with the drill guide sleeves in an engaged position with the fixation element engaged and the fixation connector.
Figure 5H:
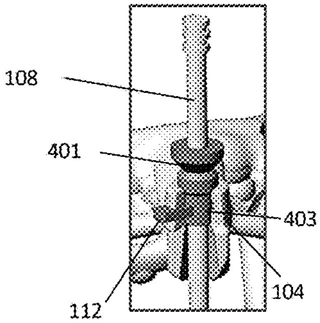
FIG. 5H is a bottom perspective view of the fixation site drill guide with the drill guide sleeve in an engaged position with the fixation element and the fixation connector.
Figure 5J:
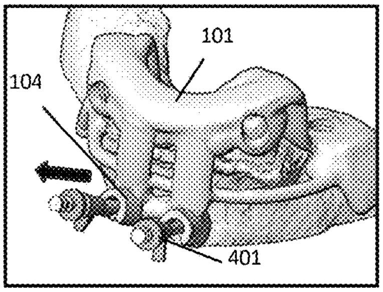
FIG. 5J is a perspective view of the fixation site drill guide mounted on the oral structure with the drill guide sleeve in a disengaged position.
Figure 5I:
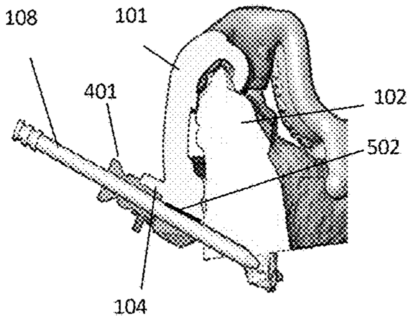
FIG. 5I illustrates a sectional view of the fixation site drill guide mounted on the oral structure with the drill guide sleeve in an engaged position with the fixation element and the fixation connector.

FIG. 5G is a partially exploded perspective view of the fixation site drill guide 101 with the drill guide sleeves 401 in an engaged position with the fixation element 104 engaged and the fixation connector 104. FIG. 5H is a sectional bottom perspective view of the fixation site drill guide 101 with the drill guide sleeve 401 in an engaged position with the fixation element 108 and the fixation connector 104. FIG. 5I illustrates a cutaway view of the fixation site drill guide 101 mounted on the oral structure 102 with the drill guide sleeve 401 in an engaged position with the fixation element 108 and the fixation connector 104. FIG. 5J is a perspective view of the fixation site drill guide 101 mounted on the oral structure 102 with the drill guide sleeve 401 in a disengaged position and the fixation element 108 illustrated as being disengaged from the fixation connector 104. The latch lock type drill guide sleeve 401 can be inserted horizontally into the fixation connector 104 on the fixation site drill guide 101 with the locking bolt 112 pointing down before or after it is positioned on the oral structure 102. By turning the locking bolt 112 into the bolt receptor 114, it can be locked to the fixation connector 104 on the fixation site drill guide 101 and prevent the drill guide sleeve 401 from sliding forward while drilling. After the fixation site drill guide 101 is positioned and the drill guide sleeve 401 is locked in position, one or more fixation sites can be drilled through the drill guide opening 105 and a fixation element 108 can be inserted into each fixation site through the drill guide opening 105. The drill guide sleeve 401 can be unlocked and pulled out of the fixation connector 104 without removing the fixation element 108 from the fixation site. The fixation site drill guide 101 can be removed from the fixation element 108 and the oral structure 102. It should be noted that after fixation site is drilled using the fixation site drill guide 101 through the drill guide sleeve 401, the fixation site drill guide sleeve(s) 401 can be removed and replaced with a latch lock type fixation element 108B, if preferred, to be used for other dental appliances 113A-F with fixation connectors 104 to complete the surgery. The latch lock type fixation element 108B is a fixation element which has a locking bolt 112 combined with fixation element 108 design and may have a wider dimension at the fixation element distal end 111. If the latch lock type fixation element 108B is to replace the drill guide sleeve 401, it should have a midsection protrusion 109 which diameter is comparable to the drill guide sleeve 401 and corresponds with the front opening of the fixation connecter 104 on the dental appliances 101, 113A-F.

Figure 6A:
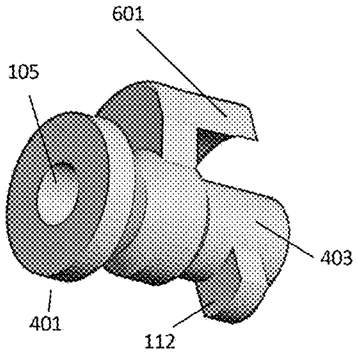
FIG. 6A is a front perspective view of a variation of a drill guide sleeve.
Figure 6B:
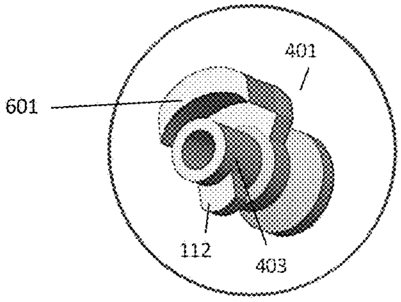
FIG. 6B is a back perspective view of the drill guide sleeve.
Figure 6C:
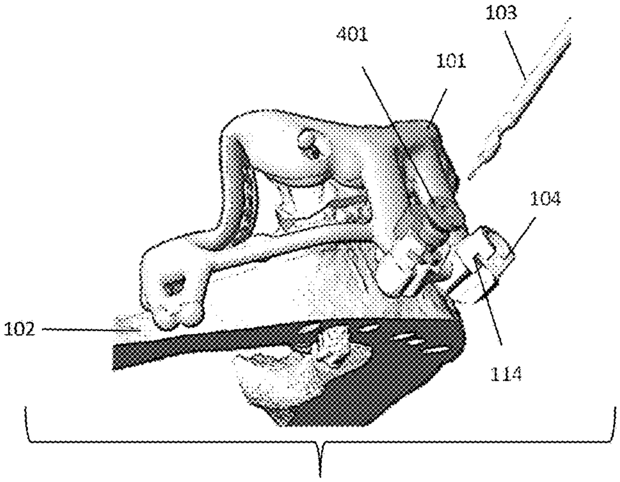
FIG. 6C is a bottom perspective view of the guide sleeve mounted in a fixation connector on a fixation site drill guide sleeve placed on an oral structure.
Figure 6D:
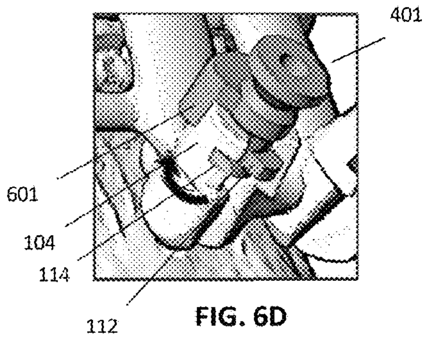
FIG. 6D is a partial view of the fixation connector and the drill guide sleeve.

FIGS. 6A-G show variations of the drill guide sleeve 401. FIG. 6A is a front perspective view of a variation of a drill guide sleeve 401. FIG. 6B is a back perspective view of the drill guide sleeve 401. This drill guide sleeve 401 is very similar to the drill guide sleeve 401 illustrated in earlier figures. The drill guide sleeve 401 includes a guide sleeve proximate end 403, a locking bolt 112 and a drill guide opening 105 as have been previously described. The drill guide sleeve 401 also includes an overhang 601 protruding out of the cylindrical body of the drill guide sleeve 401 that fits over an outer surface of the fixation connector 104. FIG. 6C is a bottom perspective view of the drill guide sleeve 401 mounted in a fixation connector 104 on a fixation site drill guide 101 placed on an oral structure 102. FIG. 6D is a partial view of the fixation connector 104 and the drill guide sleeve 401. When the drill guide sleeve 401 with the overhang 601 is inserted into the fixation connector 104, a portion of the fixation connector 104 will be pinched between a main body of the drill guide sleeve 401 and the overhang 601. The overhang 601 provides an opportunity for sturdier fixation of the drill guide sleeve 401 to the fixation connector 104 even if the width of the diameter of the opening in the fixation connector 104 is wider than the diameter of the guide sleeve proximate end 403. Once the locking bolt 112 is turned and inserted into the bolt receptor 114, the drill guide sleeve 401 would not move forward until it is unlocked.

Figure 6F:
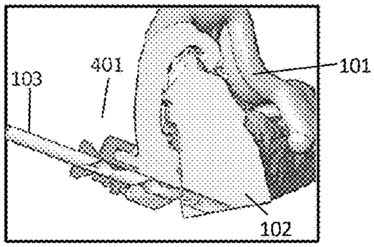
FIG. 6F is a cutaway view of the assembled drill guide insert and the fixation site drill guide receiving a drill bit for creating a fixation hole in the oral structure.
Figure 6E:
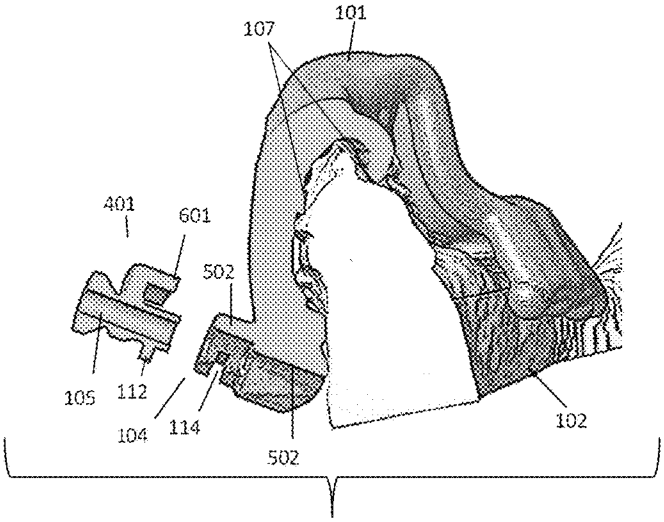
FIG. 6E is an exploded cutaway view of the fixation site drill guide positioned on the oral structure and the drill guide sleeve.
Figure 6G:
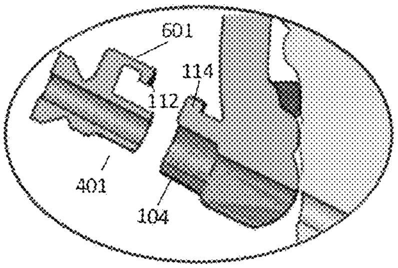
FIG. 6G is a partial exploded cutaway view of the fixation site drill guide positioned on the oral structure and the drill guide sleeve.

FIG. 6E is an exploded cutaway view of the fixation site drill guide 101 positioned on the oral structure 102 and the drill guide sleeve 401. FIG. 6F is a cutaway view of the assembled drill guide sleeve 401 and the fixation site drill guide 101 receiving a drill bit 103 for creating a fixation hole in the oral structure 102. FIG. 6G is a partial exploded cutaway view of the fixation site drill guide 101 positioned on the oral structure 102 and the drill guide sleeve 401. In FIG. 6G, the locking bolt 112 is located at the end of the overhang 601 of the drill guide sleeve 401. It can be rotated into the bolt receptor 114 created by a small blocking wall protruding outwardly from the fixation connector 104. Though the locking bolt 112 is presented in this alternative location as compared to FIG. 6E, for instance, it can be placed in multiple locations on the drill guide sleeve 401. However, if the drill guide sleeve 401 also has two locking bolts 112, the locations of both locking bolts 112 on the drill guide sleeve 401 and the bolt receptors 114 have to be coordinated with one another to avoid disturbing the insertion of drill guide sleeve 401 the fixation connector 104, and each locking bolt 112 can be sufficiently received in the respective bolt receptors 114. Though not shown, the locking bolt 112 may be located on the fixation connector 104 and the bolt receptor 114 may be located on the fixation element 108 or drill guide sleeve 401 without departing from the scope of the invention.

Figure 7A:
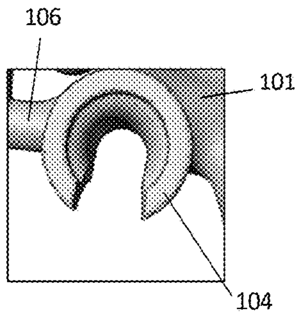
FIG. 7A is a front elevational view of the fixation connector.
Figure 7B:
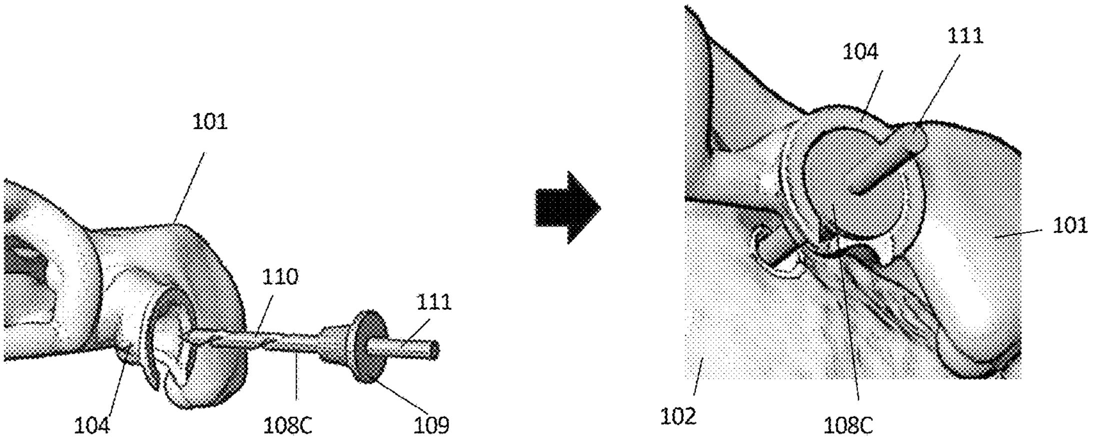
FIG. 7B is an exploded front perspective view transitioning to a sectional front perspective view of a drilling fixation element fixing a fixation site drill guide to the oral structure.
Figure 7C:
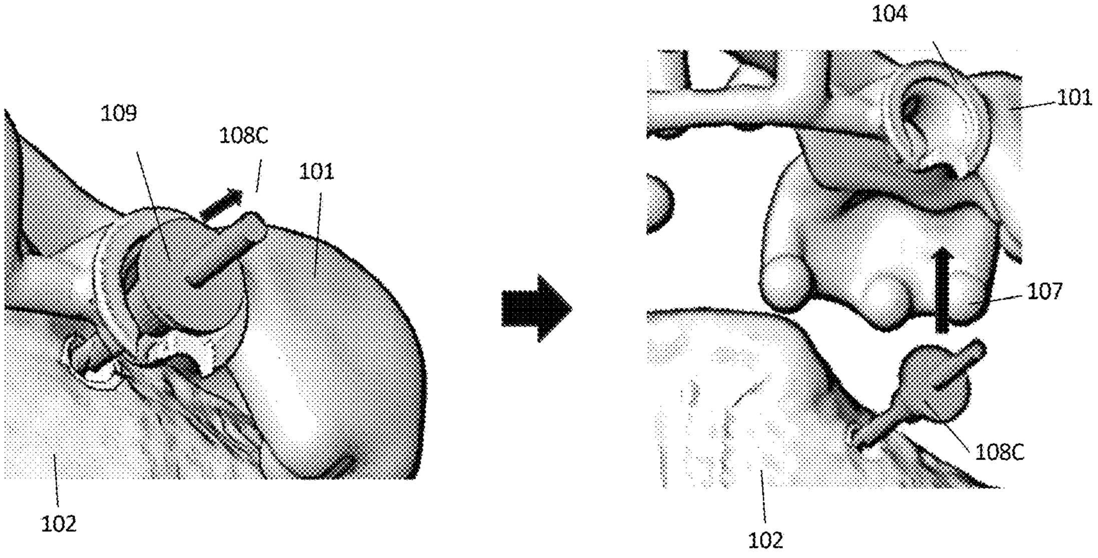
FIG. 7C is a perspective view of the drilling fixation element of FIG. 7B disengaging from the fixation site drill guide.

FIG. 7A is a front elevational view of the fixation connector 104. FIG. 7B is an exploded front perspective view transitioning to a sectional front perspective view of a drilling fixation element 108C fixing a fixation site drill guide 101 to the oral structure 102. FIG. 7C is a perspective view of the drilling fixation element 108C of FIG. 7B disengaging from the fixation site drill guide 101. FIGS. 7A-C show another variation of the exemplary fixation connector 104 that works with a drilling fixation element 108C. The drilling fixation element 108C for this fixation connector 104 has a midsection protrusion 109 that has a larger diameter than the drill bit portion and fits into an inside wall of the fixation connector 104. The drilling fixation element 108C may also have a wider diameter at the end of the midsection protrusion 109 or at the fixation element distal end 111 to stop the drilling fixation element 108C at the front surface of the fixation connecter 104. The midsection protrusion 109 may be cylindrical in part and may flare out in part. The opening of the fixation connector 104 may flare out to correspond with the shape of the midsection protrusion 109. The fixation connector 104 must present a wide enough opening for the fixation stem 110 to slide vertically through when the dental appliance 101, 113A-F is lifted out.

With this fixation connector 104 and drilling fixation element 108C, a fixation site can be drilled through the fixation connector 104 since the midsection protrusion 109 portion will be held by the fixation connector 104 as shown in FIG. 7B. If the drilling fixation element 108C is a self-tapping drill/screw, it can stay fixated to the oral structure 102 when the fixation site drill guide 101 is removed by unscrewing the drilling fixation element 108C just enough for the fixation connector 104 to be disengaged and the fixation site drill guide 101 to be lifted. Then, the next dental appliance 113A-F with one or more fixation connectors 104 can be positioned on the oral structure 102 by attaching the fixation connector 104 to drilling fixation element 108C fixated to the oral structure 102 and locked by reversing the above procedure.

FIG. 8 is a perspective view of a series of steps to engage a fixation element 108 with a fixation connector 104. In this example, the fixation connector 104 has a C-shaped face and a U-shaped stop 130B on the back side of the fixation connector 108 to work as a stopper for the midsection protrusion 109. This fixation connector 104 design with the stop 130B is more suited to be used to receive fixation elements 108 for subsequent dental appliances 101, 113A-F. At least one fixation element 108 is intended to be fixed to the oral structure 102 during the entirety of the surgical procedure. One or more fixation elements 108 may be used for some steps in the surgical procedure and not others.

FIG. 9A is a perspective view of a surgical drill guide 113B with two other different fixation connectors 104 illustrated as being lowered onto an oral structure 112 with fixation elements 108 fixed to the oral structure 102. FIG. 9B is a perspective view and a front elevational view of a fixation element 108 engaged in a snap-fit with one of the fixation connectors 108. FIG. 9C is partial side perspective views of another fixation connector 104 engaging with a drill guide sleeve 104 having a fixation element 108. The fixation connectors 104 illustrated in FIG. 9B has a simple U-shape opening and snap fit protrusions 130C on each side of the inside lateral walls of the opening. If the surgical drill guide 113B (or at least the fixation connector 104 of the surgical drill guide 113B) is made of a material that allows some flexing, the side walls of the fixation connector 104 will flex out as it pushed down on the fixation element 108, and the surgical drill guide 113B will snap onto the fixation element 108. The height and elasticity of the fixation connector 104 can be determined according to the level of desired retention. As previously mentioned, the fixation element 108 can be replaced with drilling fixation elements 108C.

The fixation connectors 104 shown in FIG. 9C has similar snap-on mechanism in cooperation with a drill guide sleeve 401. Though this feature is shown with the surgical drill guide 113B it can be on other types of dental appliances 101, 113A-F. The drill guide sleeve 401 can be used while drilling fixation holes and later to position subsequent dental appliances 101, 113A-F or it can be just used for positioning and/or locking the subsequent dental appliances 101, 113A-F after fixation holes are drilled using a fixation site drill guides 101. If the drill guide sleeve 401 is to be used on the fixation site drill guide 101, the drill guide sleeve 401 will be attached to the fixation site drill guide 101 before positioning the fixation site drill guide 101 on the oral structure 102. As shown in FIG. 9C, the fixation connector 104 has snap fit protrusions 130C configured to catch the channel portion between ribs 109B to snap onto the drill guide sleeve 401. The drill guide sleeve 401 has a drill guide opening 105 with front and back ribs 109B creating a channel which receives the fixation connector 104. The corresponding fixation connector 104 fits into the channel of the drill guide sleeves 401 and the edge of the opening of the fixation connector 108 may be tapered to snugly fit in position. It should be noted that the edge of the wall on the fixation connection 104 may be configured to wedge into the channel and stop on the inside surfaces of the front and back ribs 109B of the drill guide sleeve 401. Additionally or alternatively, the fixation connector 104 may have fixation connector walls 905 protruding from its front and back surfaces to be fit to the rim of the ribs 109B, and the fixation connector walls 905 may have a small notch or opening that can be used to insert an instrument to pop the drill guide sleeve 401 from the fixation connector 104. Optionally, the drill guide sleeve 401 may be constructed with the overhang 601 and/or locking bolt 112 previously described if the drill guide sleeve 401 has a looser fit in the fixation connector 104. One having ordinary skill in the art will understand how the two concepts can be combined. Moreover, though the drill guide sleeve 401 may be configured to snugly fit to fixation element 108, fitting the fixation element 108 loosely may provide more mobility to the guide dental appliance 101, 113A-F upon positioning before firmly connecting to the drill guide sleeve 401. If appliance protrusions 107 are strategically placed on the frame of the dental appliance 101, 113A-F, the dental appliance 101, 113A-F will not move around the fixation element 108 nor the oral structure 102 once the dental appliance 101, 113A-F is locked to the drill guide sleeve 401 firmly. Additionally, even if a subsequent dental appliance 101, 113A-F does not have any appliance protrusions 107 and the drill guide sleeve 401 initially fits loosely to the fixation element 108 before an dental appliance 101, 113A-F is placed, by having placed multiple fixation connectors 104 connecting to strategically placed fixation elements 108 with the channel type drill guide sleeves 401, the dental appliance 101, 113A-F can be repeatably and correctly positioned on the oral structure 102. However, if the drill guide sleeve 401 fits loosely to the fixation element 108 and the drill guide sleeve 401 is to be used on a fixation site drill guide 101, a drill bit 103 for drilling fixation holes should have a shank portion that fit snugly to the drill guide sleeve 401 and a smaller diameter drill portion to drill a perfect size hole (or holes) for the fixation element 108. It should be also noted that, if the drill guide sleeve 401 snugly fits to the fixation element 108, the guide sleeve proximate end 403 may be configured to contact the oral structure 102.

Figure 10A:
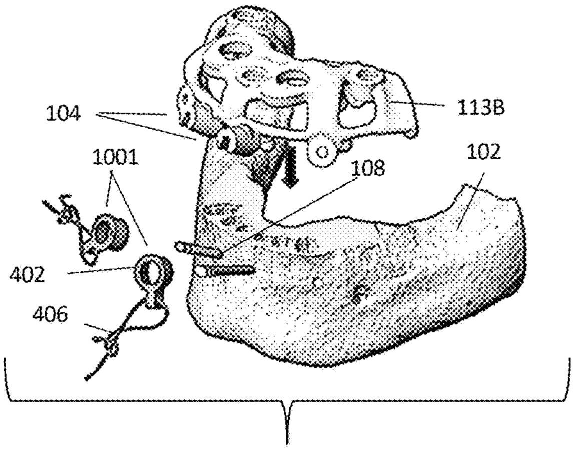
FIG. 10A is a perspective exploded view of an exemplary surgical drill guide above the oral structure and locking rings to be engaged around fixation connectors after the fixation connectors receive the fixation elements fixed to the oral structure.
Figure 10B:
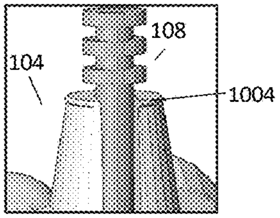
FIG. 10B is a bottom plan view of the fixation element within the fixation connector.
Figure 10D:
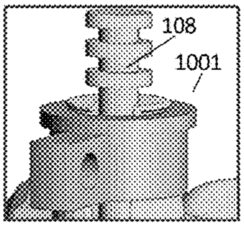
FIG. 10D is a bottom plan view of the fixation connector and fixation element of FIG. 10B with the locking ring placed around and engaged with the fixation connector.
Figure 10C:
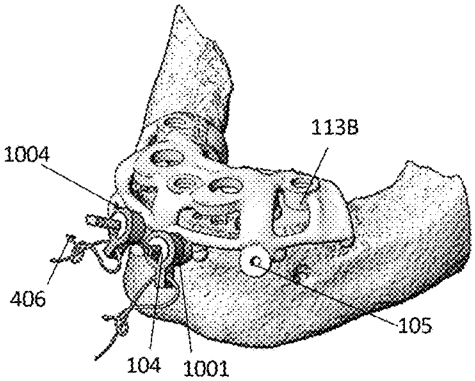
FIG. 10C is a perspective view of the assembled arrangement of FIG. 10A with the locking rings placed around the fixation connectors and the fixation elements.
Figure 10E:
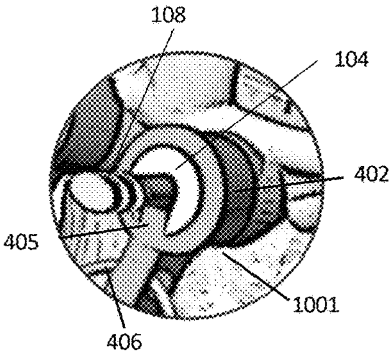
FIG. 10E is a front perspective view of a locking ring engaged with the fixation connector with the inner protrusion positioned within a gap of the fixation connector.
Figure 10F:
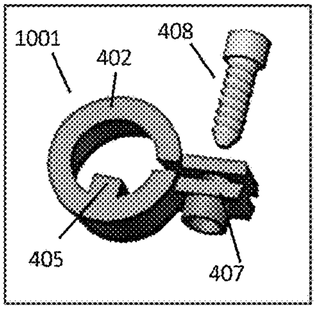
FIG. 10F is a front perspective view of a clamp-style locking ring with a ring inward protrusion.
Figure 10G:
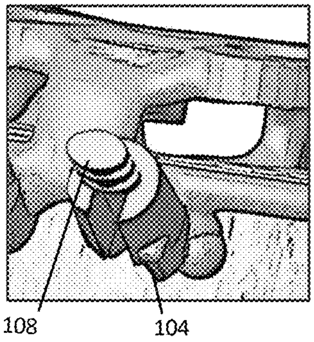
FIG. 10G is a front perspective view of a fixation connector positioned about a fixation element.
Figure 10H:
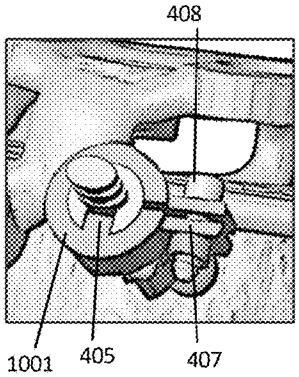
FIG. 10H is a front perspective view of the fixation connector and fixation element of FIG. 10G with the clamp-style locking ring of FIG. 10F clamped about the fixation connector and the ring inward protrusion entering a gap in the fixation connector.
Figure 10I:
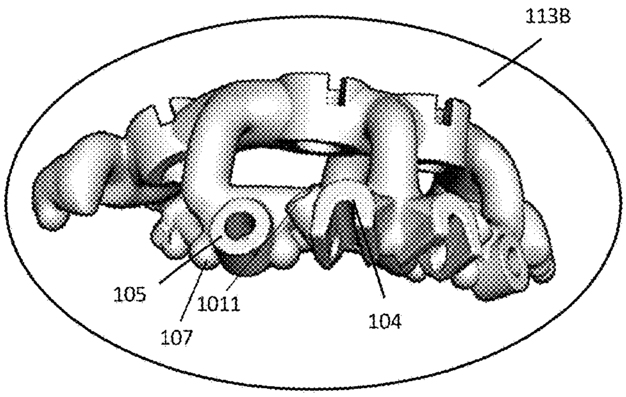
FIG. 10I is a front perspective view of an exemplary surgical drill guide.
Figure 10J:
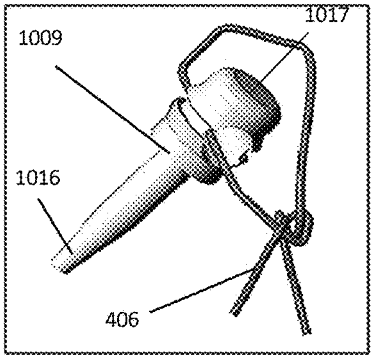
FIG. 10J is a front perspective view of a locking pin.
Figure 10K:
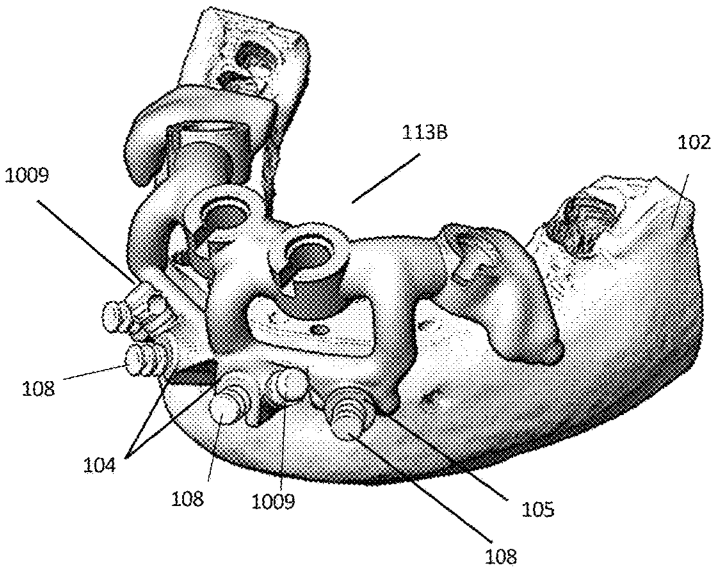
FIG. 10K is a front perspective view of the surgical drill guide of FIG. 10I engaged with the oral structure with two of the locking pins of FIG. 10J engaging the fixation connector to the fixation element in two locations and other fixation connectors fixed to the oral structure through drill guide openings.
Figure 10L:
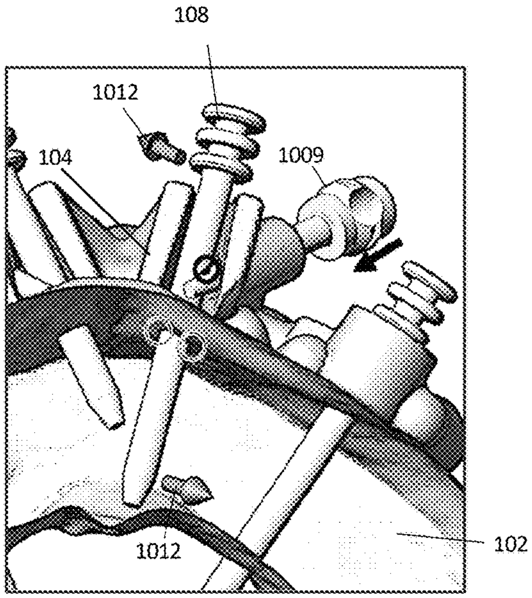
FIG. 10L is a bottom plan view illustrating directions of force when the locking pin is inserted into a side wall of the fixation connector to engage the fixation connector with the fixation element.
Figure 10M:
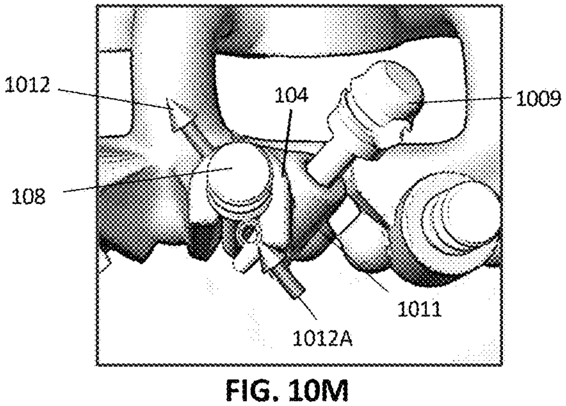
FIG. 10M is a front perspective view of the relationship in FIG. 10L illustrating directions of force from a different perspective.
Figure 10N:
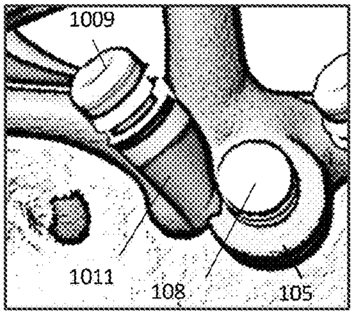
FIG. 10N is a partial front perspective view of a locking pin engaging the fixation element and the fixation connector.
Figure 10O:
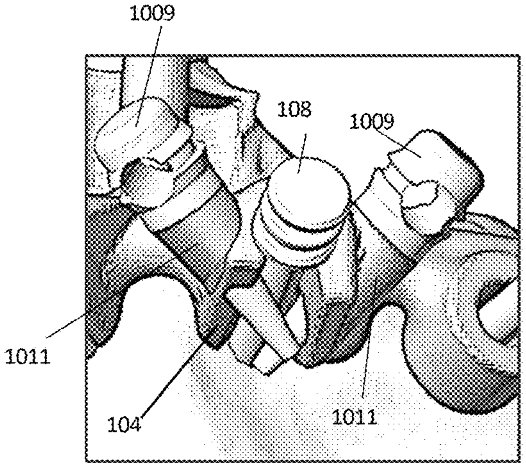
FIG. 10O is a partial bottom perspective view of a fixation element engaged to a fixation connector with two locking pins.
Figure 10P:
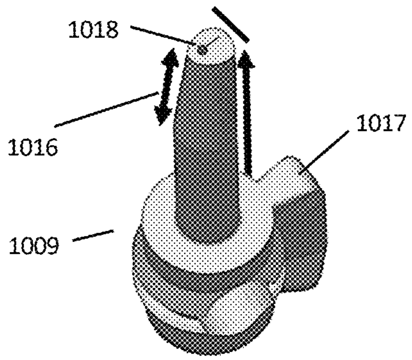
FIG. 10P is a perspective view of an embodiment of the locking pin with a tapered tip.
Figure 10Q:
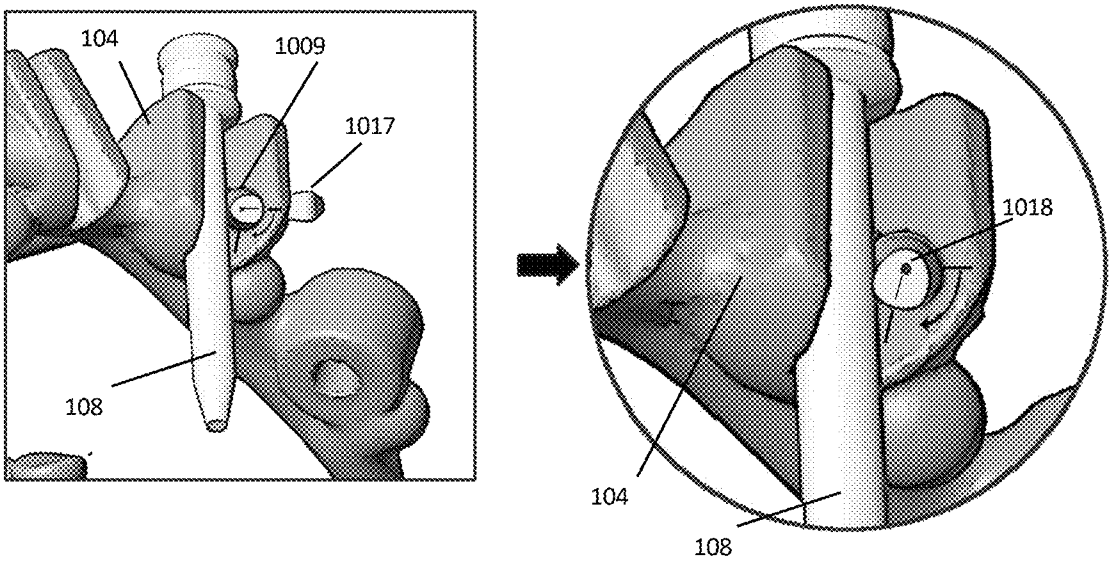
FIG. 10Q is a back-bottom perspective view of the locking pin of FIG. 10P illustrating rotation of the locking pin into an engaged position.

FIGS. 10A-Q illustrate additional exemplary variations of locking systems for dental appliances 101, 113A-F with fixation connector 104, utilizing separate components specifically designed for a locking purpose. The locking ring 1001 is an element with an opening through the middle that can be positioned onto fixation connectors 104 and/or the fixation element 108 to fix the fixation connector and fixation element in locked engagement. The locking ring 1001 is preferably made of biocompatible material. Drill guide sleeves that also meet the requirements of locking rings have been identified in this application as drill guide sleeves, but one having ordinary skill in the art will recognize that some structures are both drill guide sleeves and locking rings. The locking ring 1001 has a ring body 402 that locks a fixation connector 108 to the fixation element 108. When the locking ring 1001 is placed around the fixation connector 104 attached to the fixation element 108, the corresponding fixation connector 104 must have a depth sufficient to support the locking ring 1001.

FIG. 10A is a perspective exploded view of an exemplary surgical drill guide 113B above the oral structure 102 and locking rings 1001 to be engaged around fixation connectors 104 after the fixation connectors 104 receive the fixation elements 108 fixed to the oral structure 102. FIG. 10B is a bottom plan view of the fixation element 108 within the fixation connector 104. The ring lock 1001 locks the fixation connector 104 on a surgical drill guide 113B to the fixation element 108 fixated to the oral structure 102. As shown, the ring lock 1001 may include the ring body 402 and a string 406 attached to locking ring 1001, which will help an oral surgeon avoid dropping the locking ring 1001 past the oral cavity. The fixation connector 104 may be frustrum-shaped as illustrated in FIG. 10B. The fixation connector 104 may have a lip 1004 at the front to retain the locking ring 1001.

FIG. 10C is a perspective view of the assembled arrangement of FIG. 10A with the locking rings 1001 placed around the fixation connectors 104 and the fixation elements 108. FIG. 10D is a bottom plan view of a fixation connector 104 and fixation element 108 of FIG. 10C with the locking ring 1001 placed around and engaged with the fixation connector 104. Once the dental appliance 101, 113A-F is positioned on the oral structure 102 by attaching the fixation connector 104 to fixation element 108 pinned to the oral structure 102, the locking ring 1001 can slide over the fixation element 108 and then over the fixation connector 104. The ring body 402 may be elastic and have an opening diameter smaller than the fixation connector 104 so that the ring body 402 will squeeze the fixation connector 104 from both sides and locks the dental appliance 101, 113A-F to the fixation element 108 to the oral structure 102.

FIG. 10E is a front perspective view of a locking ring 1001 engaged with the fixation connector 104 with a ring inward protrusion 405 positioned within a gap of the fixation connector 104. With this feature, the locking ring 1001 can lock the appliance to the fixation element 108 with direct pressure on the fixation element 108. Therefore, the size of the ring body 402 may not need to be smaller than the diameter of the fixation connector 104.

FIG. 10F is a front perspective view of a clamp-style locking ring 1001 with a ring inward protrusion 405. FIG. 10G is a front perspective view of a fixation connector 104 positioned about a fixation element 108. FIG. 10H is a front perspective view of the fixation connector 104 and fixation element 108 of FIG. 10G with the clamp-style locking ring 1001 of FIG. 10F clamped about the fixation connector 104 and the ring inward protrusion 405 entering a gap in the fixation connector 104. Additionally, as shown in FIG. 10F, the locking ring 1001 may have a clamp 407 to tighten the fit of the ring body 402 with a clamp fastener 408. In this case, a generally cylindrical shape of the fixation connector 104 may be preferable to the frustrum shape.

FIG. 10I is a front perspective view of an exemplary surgical drill guide 113B. FIG. 10J is a front perspective view of a locking pin 1009. FIG. 10K is a front perspective view of the surgical drill guide 113B of FIG. 10I engaged with the oral structure 102 with two of the locking pins 1009 of FIG. 10J engaging the fixation connector 108 to the fixation element 104 in two locations and other fixation elements 108 fixed to the oral structure through drill guide openings 105. The locking pin 1009 provides another engagement mechanism to lock the fixation connector 104 into engagement with the fixation element 108 and, thereby, the dental appliance 101, 113A-F to the oral structure 102. Though the dental appliance shown is a surgical drill guide 113B, this locking system can be used on any dental appliances 101, 113A-F. With this locking system, the locking pin 1009 is inserted into a guiding passage 1011 to lock the fixation connector 104 to the fixation element 108. The locking pin 1009 may have a tapered tip 1016 and a handle 1017 with a string 406 to help the dental surgeon avoid dropping the locking pin 1009. To accept the locking pin 1009, the corresponding fixation connector 104 has a guiding passage 1011 through at least one of the side lateral walls of the fixation connector 104. The guiding passage 1011 may extend diagonally upward and outward from the side wall of the fixation connector 104 so that the exit of the guiding passage 1011 faces an opening beneath the fixation connector 104.

FIG. 10L is a bottom plan view illustrating directions of force when the locking pin 1009 is inserted into a side wall of the fixation connector 104 to engage the fixation connector 104 with the fixation element 108. FIG. 10M is a front perspective view of the relationship in FIG. 10L illustrating directions of force from a different perspective. FIG. 10N is a partial front perspective view of a locking pin 1009 engaging the fixation element 108 and the fixation connector 104. FIG. 10O is a partial bottom perspective view of a fixation element 108 engaged to a fixation connector 104 with two locking pins 1009. The guiding passage 1011 can be configured to guide the tapered tip 1016 of locking pin 1009 to be placed right below the fixation element 108 when the fixation connector 104 on the dental appliance 101, 113A-F is in position on the fixation element 108 attached to the oral structure 102. If the locking pin 1009 has a tapered tip 1016, as it is pushed through the guiding passage 1011, it will wedge the fixation element 108 upwards at the contact point (circled) against an inside wall of the fixation connector 104 in the direction shown with dimensional arrows 1012. The locking pin 1009 will tightening the fit of the dental appliance 101, 113A-F to the fixation element 108. Moreover, when the fixation element 108 is pushed by the locking pin 1009, the point where the fixation element 108 enters the cortical bone of the oral structure 102 becomes a fulcrum point (circled), and the fixation element 108 will be pushed towards the opposite direction as an arrow 1012 shows, securing the fixation element 108 further to the oral structure 102. It should be noted that the fixation connector 104 may have a single guiding passage 1011 on through both side walls to accept a locking pin 1009 across the fixation connector 104. A single fixation connector 104 may also have more than one guiding passage 1011 aligned with its walls to allow multiple locking pins 1009 to engage one fixation element 108. As illustrated in FIG. 10N, a locking pin 1009 may be used to engage a fixation element 108 within a drill guide opening 105 just to tighten the fit.

FIG. 10P is a perspective view of an embodiment of the locking pin 1009 with an off-center tapered tip 1016. FIG. 10Q is a back-bottom perspective view of the locking pin 1009 of FIG. 10P illustrating rotation of the locking pin 1009 into an engaged position. As shown, the tapered tip 1016 of this locking pin 1009 may be tapered on one side or may have different tapering on different sides. The locking pin 1009 may also have a marking 1018 that helps identify the orientation of the tapering. Additionally, it may have a handle 1017 on its head. The position of handle 1017 may be placed to indicate the non-tapered side like this figure or to indicate the tapered side.

The locking pin 1009 can be inserted through a guiding passage 1011 to lock the fixation element 108 to the fixation connector 104 and to the oral structure 102. When this locking pin 1009 with an off-center taper 1016 is used, it can be inserted through the guiding passage 1011 so that the tapered side is nearest the fixation element 108 as illustrated. By pushing the locking pin 1009 against the surface of the fixation element 108, it will tighten the engagement as previously explained. Then, by rotating the locking pin 1009, as illustrated, the locking pin 1009 will turn the non-tapered side of the locking pin 1009 to about the fixation element 108 and tighten the engagement further.

Figure 11A:
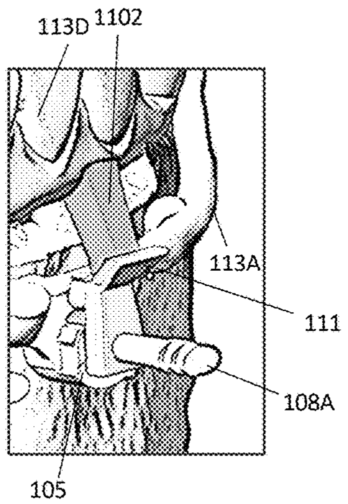
FIG. 11A is a partial front perspective view of a fixation element engaged with the drill guide opening.

FIG. 11A shows a partial front perspective view of a fixation element 108A engaged with the fixation connector

Figure 11B:
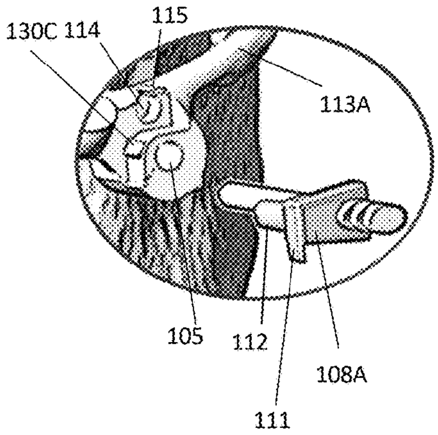
FIG. 11B is a partial front exploded perspective view of the fixation element of FIG. 11A removed from the drill guide opening.
Figure 11C:
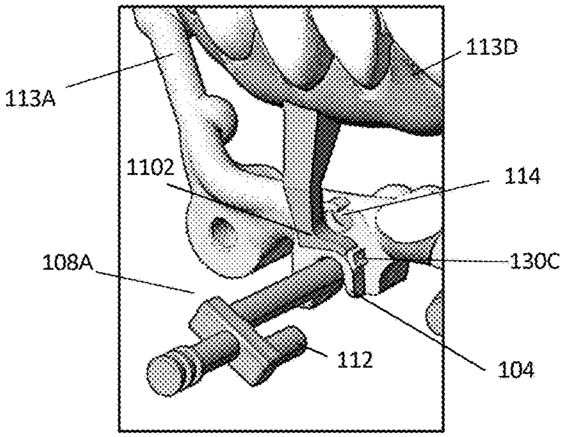
FIG. 11C is a partial front perspective view of the fixation element shown in FIG. 1B and the dental restoration stacked on the bone reduction jig with the bone reduction jig having the fixation connector.
Figure 11D:
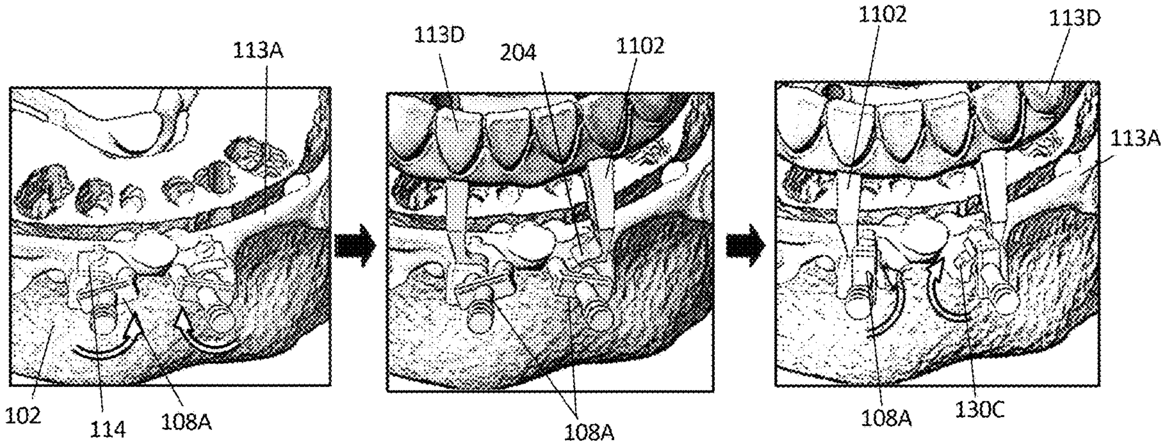
FIG. 11D is a series of front perspective views illustrating the fixation elements engaged with the bone reduction jig and the locking bolts rotating into engagement with a dental restoration.

104 with a stackable dental appliance assembly with a drill guide opening 105 on the bone reduction jig 113A. FIG. 11B is a partial front exploded perspective view of the fixation element 108A of FIG. 11A removed from the drill guide opening 105. FIG. 11C is a partial front perspective view of the fixation element 108A shown in FIG. 11B and a stackable dental appliance assembly 113A/113D with the bone reduction jig 113A serving as the base frame having the fixation connector 104. FIG. 11D is a series of front perspective views illustrating the fixation elements 108A engaged with the bone reduction jig 113A and the locking bolts 112 rotating into engagement with a dental restoration 113D. As shown, the bolt lock type fixation element 108A can be inserted into either a drill guide opening 105 of the bone reduction jig 113A with the dental restoration 113D stacked on top or the fixation connector 104. Both the drill guide opening 105 and the fixation connector 104 have the same corresponding bolt receptor 114 and the snap fit protrusion 130C, similar to FIG. 1F. When the bolt lock type fixation element 108A is used with stacked dental appliances 101, 113A-F, it can be used not only to fixate the base frame to the oral structure but also engage the superstructure to the base frame. FIG. 11D illustrates steps for engaging two dental appliances 113A/113D. The bolt lock type fixation element 108A is engaged with the oral structure 102 and locks the bone reduction jig 113A in place by positioning the locking bolt 112 on the snap fit protrusion 130C. The dental restoration 113D is positioned on the bone reduction jig 113A by placing the connector legs 1102 on the designated position on the fixation connector 104 of the bone reduction jig 113A. The dental restoration 113D is solidly connected to the bone reduction jig 113A by turning and inserting the locking bolt 112 into the bolt receptor 114 on the fixation connector 104, trapping the connector legs 1102.

FIG. 12A-FIG. 25B illustrate variations of dental appliances 101, 113A-F and the parts in a dental guide set that uses fixation elements 108 and optional features.

Figure 12A:
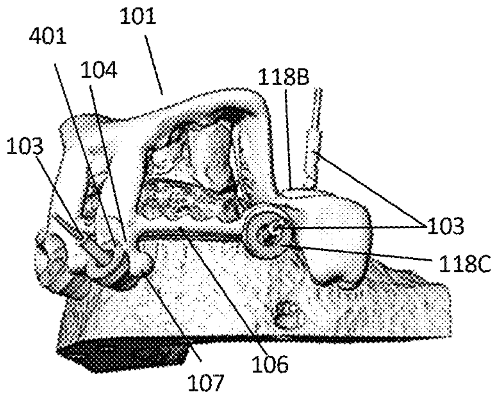
FIG. 12A is a front side perspective view of a fixation site drill guide with a plurality of drill bits sitting in locations for drilling the oral structure.
Figure 12B:
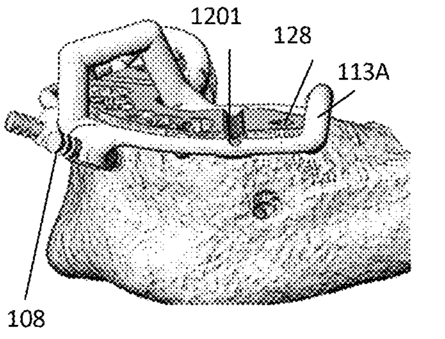
FIG. 12B is a side perspective view of the oral structure with created rest marker holes and a horizontal slit marker shown with an exemplary bone reduction jig.

FIG. 12A is a front side perspective view of a fixation site drill guide 101 with a plurality of drill bits 103 sitting in locations for drilling the oral structure 102. FIG. 12B is a side perspective view of the oral structure 102 with created horizontal recesses 1201 and a horizontal slit marker shown with an exemplary bone reduction jig 113A. FIG. 12A shows a fixation site drill guide 101 that has additional horizontal drill guide hole 118C and vertical drill guide hole 118B. The vertical drill guide hole 118B can be used to create a positioning hole 128 for use as a marker/receptor for other dental appliances 113A-F, to have a positioning post 125 or to accept a positioning pin 1501 (See FIGS. 15A and 15B) that can be inserted into the positioning hole 128. The horizontal drill guide hole 118C can become a horizontal recess 1201 that marks the bone reduction level. Though this exemplary fixation site drill guide 101 has a support bar 106 that can be used to mark the bone reduction line, the horizontal recess 1201 will reach the lingual side of the oral structure 102. The surgeon just needs to reduce the bone until the horizontal drill guide hole 118C appears from the facial side to the lingual side of the oral structure 102 as illustrated in FIG. 12B. After the fixation site drill guide 101 is removed from the oral structure 102 and bone is roughly reduced according to the created markings, a bone reduction jig 113A can be positioned on the fixation element 108 and the oral structure 102. This exemplary bone reduction jig 113A may have a small marking that can be aligned with the horizontal recess 1201. The exemplary bone reduction jig 113A may also have a handle for ease of use. Here, engagement of the fixation element 108 and the fixation connector may be the fixation connector 104 resting on the fixation element 108. The horizontal drill guide hole 118C can be used for a fiducial marker to be scanned with the oral structure 102 before making significant changes to the oral structure 102 and to be scanned with fiducial markers on the installed implants later. The design of this fixation site drill guide 101 with large open view for the oral structure 102 is beneficial for positioning, can be used for extra scanning as previously mentioned, and can be incorporated into a stackable guide set.

Figure 13A:
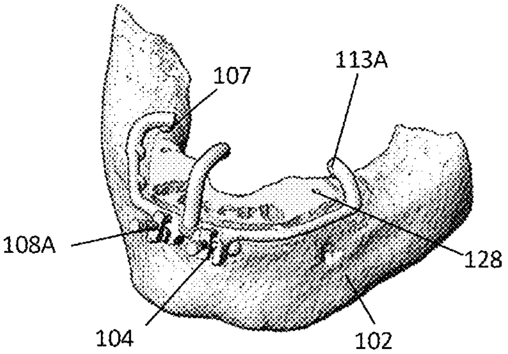
FIG. 13A is a top front perspective view of a bone reduction jig fixed to the oral structure.

FIG. 13A is a top front perspective view of a bone reduction jig 113A fixed to the oral structure 102. The bone reduction jig 113A in FIG. 13A is similar to the bone reduction jig 113A in FIG. 1C but with a handle and without a support bar 106 on the lingual side. Though this bone reduction jig 113A has appliance protrusions 107 that rest on the posterior ridge areas, if the bone reduction jig 113A is attachable and lockable to the fixation elements 108A using fixation connectors 104, the appliance protrusions 107 resting on the ridge of the bone may be superfluous and the bone reduction jig 113A may be little more than a bar on the facial side.

Figure 13B:
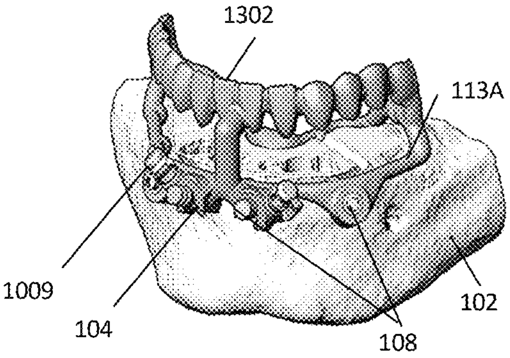
FIG. 13B is a top front perspective view of a restoration model fixed to the oral structure.

FIG. 13B shows a bone reduction jig 113A stacked with a modified final restoration model 1302 with veneered teeth having a facial surface of the planned restoration configured to be positioned in the planned location in the mouth. This type of bone reduction jig 113A may be used when the surgeon does not want to use a surgical drill guide 113B, but needs a guide for adjusting/reducing the bone. After a fixation site or sites are drilled and a fixation element 108 is inserted into the oral structure 102, the bone reduction jig 113A can be positioned on the oral structure 102 and the bone can be adjusted as with any bone reduction jig 113A. If the surgeon drills osteotomies for implant sites without a surgical drill guide 113B, the modified planned restoration model 1302 attached to the bone reduction jig 113A can be used as a guide to decide where to drill osteotomies. It should be noted that, though the bone reduction jig 113A has veneered teeth as a modified restoration model 1302, the teeth may be modified differently (shelled, partially veneered, etc.) without departing from the scope of the inventive disclosure.

Figure 14A:
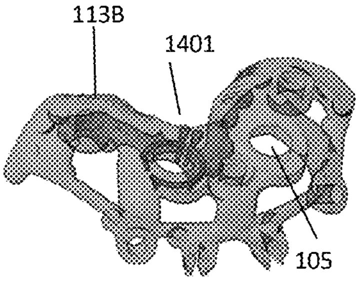
FIG. 14A is a top back perspective view of an irrigation spout inside of a surgical drill guide.
Figure 14B:
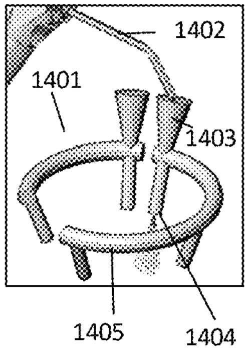
FIG. 14B is a perspective view of the irrigation spout of FIG. 14A.

FIG. 14A is a top back perspective view of an irrigation spout 1401 inside of surgical drill guide 113B. FIG. 14B is a perspective view of the irrigation spout 1401 of FIG. 14A. The additional optional feature of irrigation spout 1401 helps spray irrigation liquid under a drill guide opening 105 around the osteotomy site. The irrigation spout 1401 has at least one funnel 1403 that receives water from a water source 1402 for irrigation liquid and at least one sprayer 1404 that sprays irrigation liquid on the osteotomy site. It may also have a tube 1405 that distributes irrigation liquid to multiple sprayers 1404. The irrigation spout 1401 can be placed inside of the surgical drill guide frame 113B or built into the frame of a surgical drill guide 113B with only the funnel 1403 open to the top surface so that the funnel 1403 can accept water from the water source 1402.

Figure 15A:
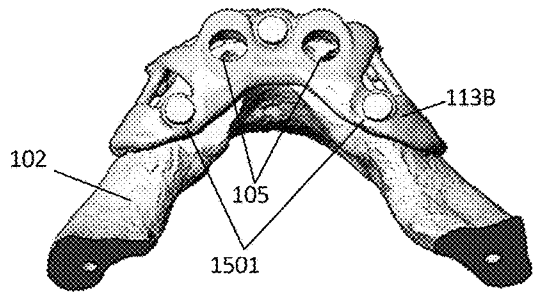
FIG. 15A is a top back perspective view of a surgical drill guide fixed to the oral structure.
Figure 15B:
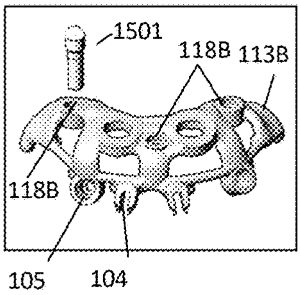
FIG. 15B is a front perspective view of the surgical drill guide of FIG. 15A with a positioning pin hovering over a positioning pin opening.
Figure 15C:
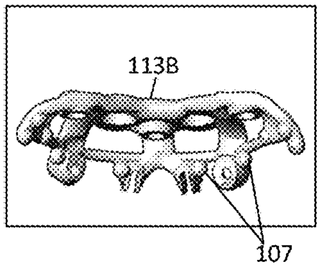
FIG. 15C is a back perspective view of the surgical drill guide of FIG. 15A.

FIG. 15A is a top back perspective view of a surgical drill guide 113B fixed to the oral structure 102. FIG. 15B is a front perspective view of the surgical drill guide 113B of FIG. 15A with a positioning pin 1501 hovering over a vertical drill guide opening 118B. FIG. 15C is a back perspective view of the surgical drill guide 113B of FIG. 15A. If the surgical drill guide 113B does not have any lingual lateral contact with the oral structure 102, the surgical drill guide 113B can be positioned on the oral structure 102 using solely the fixation connector 104 and fixation element 108 or other means previously described herein. Although a surgical guide 113B tends to tip while drilling without lingual support, vertical drill guide hole 118B may receive a positioning pin 1501 into the positioning hole 128 to address this problem. If the positioning hole 128 is created with the surgical drill guide 113B, manually holding the surgical drill guide 113B in position while drilling may be recommended. Alternatively, a natural hole such as a root socket may be used to insert a positioning pin 1501. By horizontally and vertically fixating the surgical guide 113B to the bone, the appliance can be solidly attached to the bone.

Figure 15D:
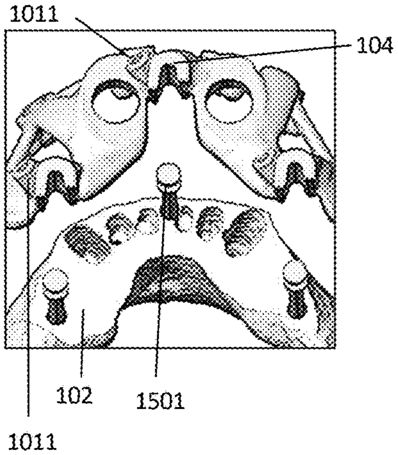
FIG. 15D is a top exploded perspective view of a surgical drill guide with positioning pins inserted in the oral structure.
Figure 15E:
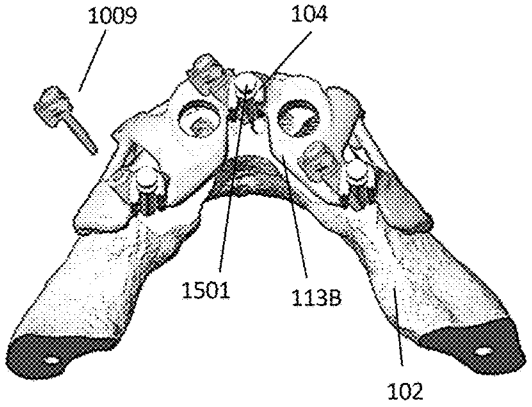
FIG. 15E is a top perspective view of the surgical drill guide with the positioning pins in the oral structure.
Figure 15F:
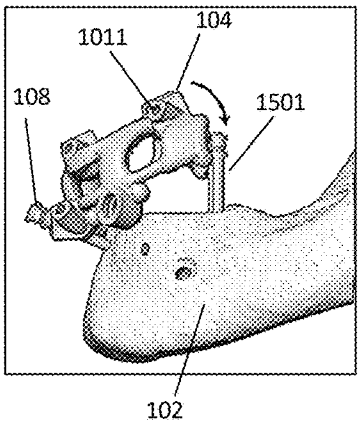
FIG. 15F is a side exploded perspective view of a surgical drill guide with a positioning pin inserted in the oral structure.

FIG. 15D is a top exploded perspective view of a surgical drill guide 113B with positioning pins 1501 inserted in the oral structure 102. FIG. 15E is a top perspective view of the surgical drill guide 113B with the positioning pins 1501 in the oral structure 102. FIG. 15F is a side exploded perspective view of a surgical drill guide 113B with a positioning pin 1501 inserted in the oral structure 102. Alternatively, instead of the vertical drill guide hole 118B, the surgical drill guide 113B may have the fixation connector 104 on a top surface positioned to have an opening generally facing lingually as shown in FIG. 15D. If the hole needs to be drilled with the same surgical drill guide 113B, drill guide sleeve 401 can be locked on to the top fixation connector 104 to drill vertically into the oral structure 102. If the hole has been drilled previously and the positioning pin 1501 is inserted into the hole to place the surgical drill guide 113B on the oral structure 102, begin by positioning the front fixation connector 104 on the fixation element 108 at a slight incline, aligning the top fixation connector 104 to the positioning pin 1501 as illustrated in FIG. 15F. The surgical drill guide 113B can be tilted down into position, and the fixation connectors 104 can be locked with one of the disclosed engagement mechanisms. With the surgical drill guide 113B in FIG. 15B, the top fixation connectors 104 can be securely locked to the positioning pin 1501, using locking pins 1009 with partially tapered tip 1016. It should be also noted that, instead of the horizontally inserted front fixations elements 108, the vertically inserted positioning pin 1501 can be used to fix dental appliances 101, 113A-F, and the fixation connector 104 placed on the top surface of the dental appliance 101, 113A-F along with previously described locking systems may be used for engagement.

Figure 15G:
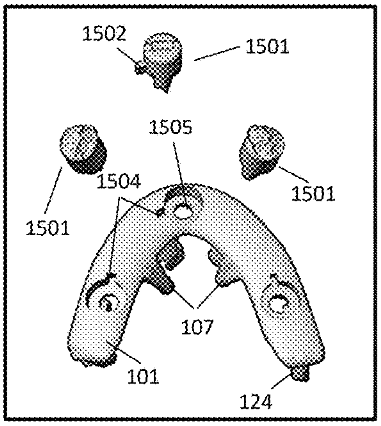
FIG. 15G is a top exploded perspective view of positioning pins with a fixation site drill guide.
Figure 15H:
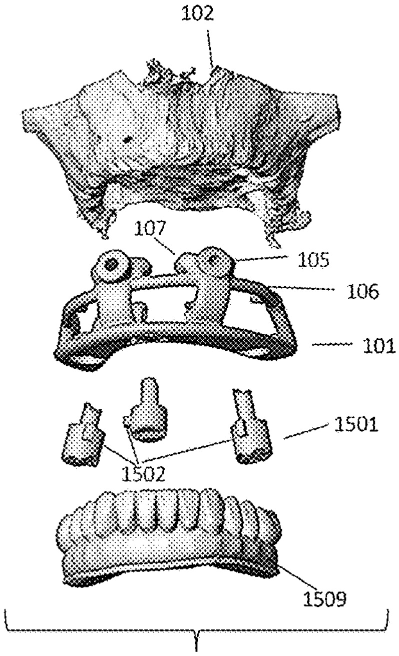
FIG. 15H is a front exploded perspective view of the fixation site drill guide between a top and bottom oral structure.
Figure 15I:
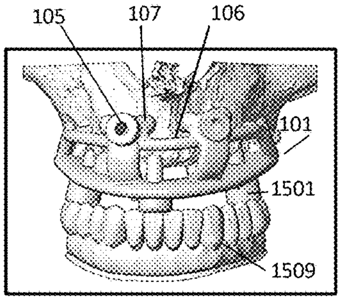
FIG. 15I is a front perspective view of the fixation site drill guide illustrated in FIG. 15H.

FIG. 15G is a top exploded perspective view of positioning pins 1501 with a fixation site drill guide 101. FIG. 15H is a front exploded perspective view of the fixation site drill guide 101 between a top oral structure 102 and mandible opposing oral structure 1509. FIG. 15I is a front perspective view of the fixation site drill guide 101 illustrated in FIG. 15H. These figures show a variation of the positioning pin 1501 with a fixation site drill guide 101 for a fully edentulous case. In exemplary assembly, besides the drill guide opening 105, appliance protrusions 107 and fixation site support bar 106 (optional), the fixation site drill guide 101 has one or more pin receptors 1505 which may also work as drill guide openings 105 for creating positioning holes 128. Each pin receptor 1505 may have a shoulder area around the through hole. The shoulder area has a diameter larger than the pin receptor 1505 and is configured to receive the head portion of the positioning pin 1501. It may also have an alignment marker receptor 1504 which accepts an alignment marker 1502 on the positioning pin 1501 to help align the bite impression portion in the right direction. The positioning pin 1501 may have a head portion that has a larger diameter than its pin portion, the tip of which may be configured to rest on the oral surface like these exemplary positioning pins 1501 instead of being inserted into a hole on the oral structure 102. Though it is not illustrated, if there are multiple positioning pins 1501 with same size head portions, the positioning pins 1501 may be numbered or similarly uniquely marked, and the top frame of the fixation site drill guide 101 may have corresponding markings near the corresponding pin receptor 1505. Additionally, the positioning pin 1501 may have a bite impression of the occluding part of the opposing oral structure on top of its head portion, which helps position the fixation site drill guide 101 on the oral structure 102.

With this type of assembly, each positioning pin 1501 can be inserted into the corresponding pin receptor 1505 on the fixation site drill guide 101, and the assembled fixation site drill guide 101 can be positioned on the oral structure 102. If necessary, let the patient bite against the bite impression(s) to properly position the fixation site drill guide 101. Then fixation site(s) can be drilled through the fixation site drill guide openings 105. It should be noted that, though this exemplary fixation drill guide 101 has drill guide openings 105, it may have fixation connectors 104 instead, in cooperation with drill guide sleeves 401. Optionally, one or more positioning holes 128 can be drilled thorough the pin receptor 1505 to be used with subsequent dental appliance(s) 113A-F.

Figure 16B:
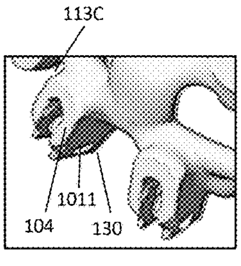
FIG. 16B is a partial perspective view of the transfer jig of FIG. 16A focused on two fixation connectors.
Figure 16C:
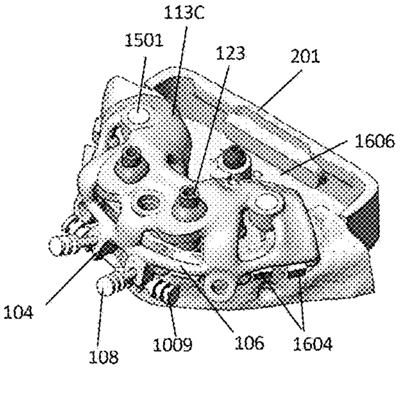
FIG. 16C is a top side perspective view of a transfer jig with an oral structure of a model base.
Figure 16A:
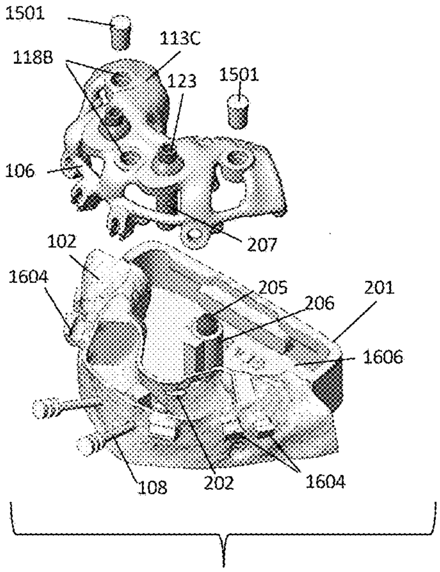
FIG. 16A is a top side exploded perspective view of a transfer jig with an oral structure of a model base.

FIG. 16A is a top side exploded perspective view of a transfer jig 113C with an oral structure 102 of a model base 201. FIG. 16B is a partial perspective view of the transfer jig 113C of FIG. 16A focused on two fixation connectors 104. FIG. 16C is a top side perspective view of a transfer jig 113C with an oral structure 102 of a model base 201. The exemplary model base 201 is digitally designed based on a scan of the oral structure 102 stored in the master data file combined with a tub design similar to another variation of model base 201 shown in FIG. 18*b*, and its design coordinates can be stored along with coordinates of the dental appliance designs such as the design coordinates of the transfer jig 113C. Though a part of this model base 201 has an artificial oral structure 102 modeled after the scanned oral structure 102 of the patient to accept the transfer jig 113C, the shape of the artificial oral structure 102 can be modified according to the expected locations of implant analogs 207 when the transfer jig 113C is attached to the model base 201. The model base 201 has a hollowed tub section in the area where the implant analogs 207 will be received. The hollowed tub section may have one or more model windows 202 that opens to an overflow tub section 1606 for catching overflow of a model material 209 when it is poured. Additionally, the model base 201 may have connectors such as one or more base tabs 1604 that accept fixation site lateral bar 106 of the transfer jig 113C, one or more simulated fixation element 108 that accept the fixation connectors 104 on the transfer jig 113C, one or more threaded model connectors that can be for the transfer jig 113C as well as a dental restoration 113D. As previously mentioned, the exemplary transfer jig 113C may have some of the functionality of a surgical drill guide 113B with vertical drill guide openings 118B for creating positioning holes 128 that receive positioning pins 1501 that rest on the model base 201. As shown on the exemplary the transfer jig 113C on FIG. 16B, the walls of the fixation connectors 104 may have a guiding passage 1011. After the transfer jig 113C is positioned on the model base 201, a locking pin 1009 can be horizontally inserted into the guiding passage 1011 of each fixation connector 104 to lock the transfer jig 113C to the model base 201. However, a fixation connector 104 may have a pin lock hole through the guiding passage 1011 extending diagonally upwards from the side lateral wall of the fixation connector 104 that accepts a locking pin 1009 to secure the transfer jig 113C to the simulated fixation element 108 on the model base 201.

Figure 17A:
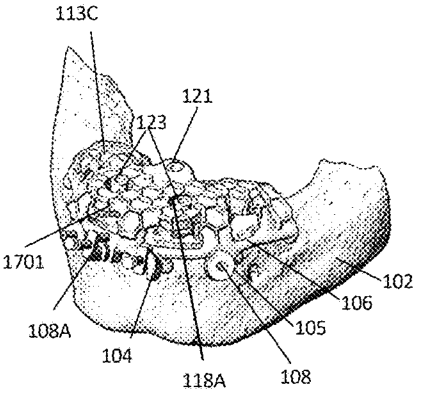
FIG. 17A is a front perspective view of a transfer jig placed on an oral structure.
Figure 17C:
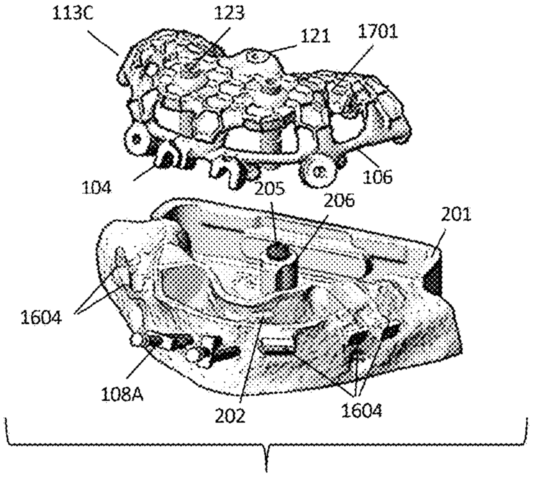
FIG. 17C is an exploded view of the and transfer jig mounted on the model base.
Figure 17B:
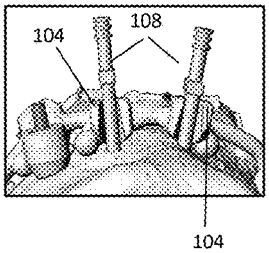
FIG. 17B is a bottom view of a portion of the transfer jig of FIG. 17A with fixation connectors fixed by fixation elements.

FIG. 17A is a front perspective view of a transfer jig 113C placed on an oral structure 102. FIG. 17B is a bottom view of a portion of the transfer jig 113C of FIG. 17A with fixation connectors 104 fixed by fixation elements 108. FIG. 17C is an exploded view of the and transfer jig 113C mounted on the model base 201. These figures illustrate another variation of a transfer jig 113C which has some of the functionality of a surgical drill guide 113B. The transfer jig 113C has the fixation connectors 104 which accepts bolt-lock type fixation elements 108. As shown in FIG. 17B, the fixation connector 104 may have an extended support wall and flared out opening. The transfer jig 113C may have a restoration connector 121 on the lingual side connectable to the threaded model connector 205 on the model base 201. The transfer jig 113C in this illustration has a scan pattern 1701 on a top surface to enhance scanning. Scan bodies can be attached to the installed implants and if the oral structures 102 are scanned after surgery using an inter-oral scanner or photogrammetry camera, the scan pattern 1701 on the transfer jig 113C will help align a scan data file to a pre-operative master data file. The transfer jig 113C can function as a physical transfer jig to make a physical master implant model 210 by transferring positional index of installed implants to a model base 201. The exemplary model base 201 has bolt lock type fixation element 108A to lock the transfer jig 113C to the model base 201.

Figure 17E:
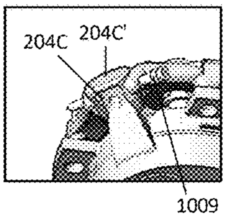
FIG. 17E is a partial bottom perspective view of the transfer jig.
Figure 17D:
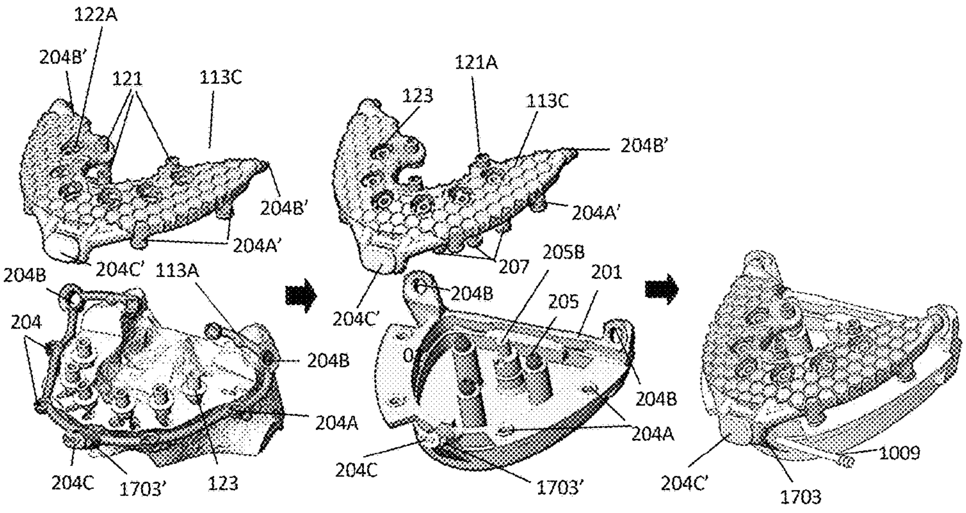
FIG. 17D is a series of perspective figures illustrating how the bone reduction jig and transfer jig operate as a stackable guide set and used to create a master implant model.

FIG. 17D is a series of perspective figures illustrating how the bone reduction jig 113A and transfer jig 113C operate as a stackable guide set to create a master implant model 210. FIG. 17E is a partial bottom perspective view of the transfer jig 113C. The stackable transfer jig 113C is attachable to the bone reduction jig 113A. Though any type of connectors can be used to connect the transfer jig 113C to the bone reduction jig 113A, this figure illustrates three types of connectors: (1) magnetic model connectors 204A on the bone reduction jig 113A connectable to the corresponding magnetic connectors 204A' on the transfer jig 113C, (2) back horizontal connectors 204B connectable to the corresponding back horizontal connectors 204B' on the transfer jig 113C, (3) a front handle connector 204C connectable to the corresponding front handle connector 204C' on the transfer jig 113C. When referencing stackable dental guide sets, the dental appliance 101, 113A-F nearest the oral structure 102 is identified as the base frame and the next dental appliance 101, 113A-F is identified as the superstructure. FIG. 17D illustrates the bone reduction jig 113A as the base frame and the transfer jig 113C as the superstructure. The same connection elements that connected the base frame and superstructure in this figure can be used with other stackable guide sets without departing from the scope of the invention, as will be recognized by one with ordinary skill in the art.

The front handle connector 204C' on the transfer jig 113C may have a bottom and back openings so that it can be attached to the stackable bone reduction jig 113A by tilting down and sliding into the front handle connector 204C at the same time connecting the back horizontal connectors 204*b*' to the back horizontal connectors 204B on the bone reduction jig 113A. The transfer jig 113C may also have a guide passage 1011 on the side walls that align with the through hole 1703 on the side of the front handle connector 204C of the bone reduction jig 113A to accept a locking pin 1009. The transfer jig 117 has a scan pattern 1701 that helps if the scanning or photogrammetry process is done with scan-bodies on the installed implants. Additionally, it can be used as a physical transfer jig 113C if implant sleeve 123 are glued to the receptor holes 122A and picked up with the transfer jig 113C and transferred to a model base 201 as shown in FIG. 17D. The transfer jig 113C will be attached to a model base 201 by attaching its connectors 204A', 204B' and 204C' to the corresponding connectors 204A, 204B and 204C on the model base 201. Moreover, if the transfer jig 113C physically transfers the positional index to a model base 201 to create a master implant model 210, the transfer jig 113C may also have one or more restoration connectors 121 connectable to the corresponding threaded model connectors 205 on the model base 201. After the transfer jig 113C is positioned on the model base 201, a locking pin 1009 can be inserted into the aligned through holes 1703 on the front handles of transfer jig 113C and the model base 201 as shown in FIG. 17E. The locking pin 1009 along with back horizontal connectors 204B and 204B' should lock the transfer jig 113C to the model base 201 sufficiently, but restoration connectors 121 and threaded model connectors 205 can be secured as well. As previously explained, the bolt lock type fixation element 108A may be used as a connecting and locking system for a stackable guide set. Moreover, other appliance designs and features disclosed for the sequential guide systems may be also applicable to a stackable type of guide set.

With respect to obtaining a digital implant model, the methods that are very similar to previously explained [Method 1]-[Method 4] can be used for a stackable type of guide drill guide system also as previously explained with the sequential guide system procedure though naming of some part may be different. Regarding the [Method 4], if the digital positional index of installed implants is taken by scanning the patient's mouth with scan bodies attached to the installed implants while the base frame of the stackable guide set is still attached to the oral structure, the actual implant positions can be aligned to the preoperative master data file which includes preoperative scan data and appliance designs oriented to the scan data by aligning the 3D coordinates of the base frame to the corresponding coordinates of its design in the preoperative master data file as is known in the art. Optionally, a detachably attachable transfer jig 113C like the one described in FIG. 17D or other scan attachment can be placed on the base frame to be included in the scan also. To adjust small deviation that may occur during positioning of base frame, after the base frame is positioned and fixated in the mouth, an extra scan of the patient's mouth before making any significant changes to the oral structure 102 can be taken and any necessary positional adjustment can be made as previously explained. A positioning attachment can also stay attached to the base frame during the extra scan if it provides enough visibility of the oral structure, but it is not necessary. If the positioning attachment has one or more vertical drill guides for positioning holes 128, one or more positioning pins 1501 or scan bodies may be placed in the positioning hole 128 to be scanned with the base frame to be included in the extra scan for adjustment of positional deviation.

Figure 18A:
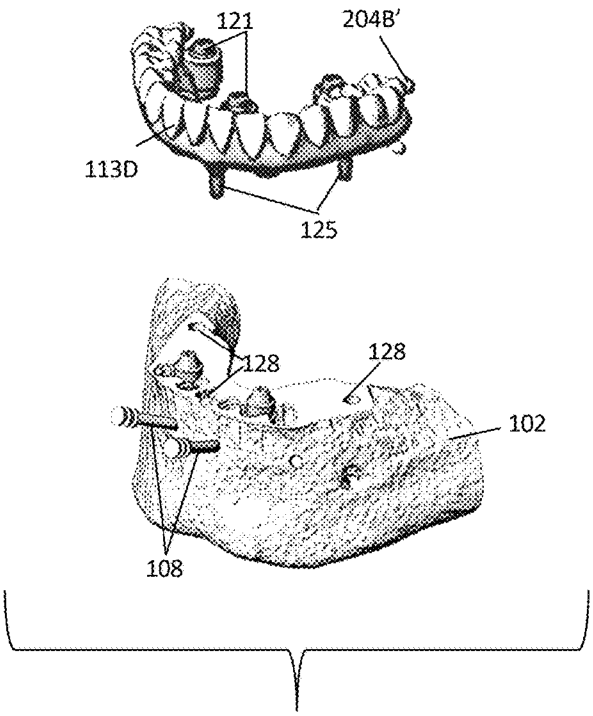
FIG. 18A is an exploded perspective view of an exemplary dental restoration and oral structure.
Figure 18B:
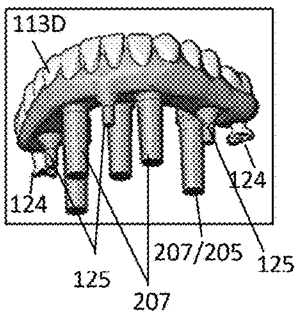
FIG. 18B is a bottom perspective view of the dental restoration after positional index of installed implants are taken.
Figure 18C:
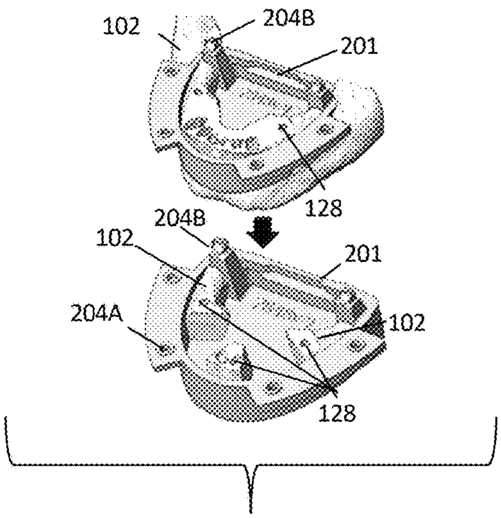
FIG. 18C is a perspective view, illustrating refinement of a model base.
Figure 18D:
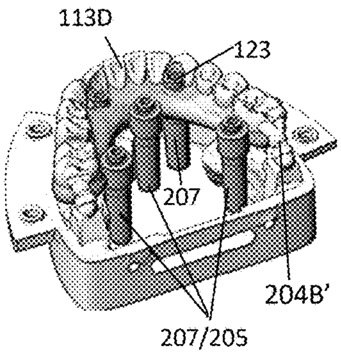
FIG. 18D is a back perspective view of the assembled structure of FIGS. 18B and 18C.

FIG. 18A is an exploded perspective view of an exemplary dental restoration 113D and oral structure 102. FIG. 18B is a bottom perspective view of the dental restoration 113D after positional index of installed implants are taken. FIG. 18C is a perspective view illustrating refinement of a model base 201. FIG. 18D is a back perspective view of the assembled structure of FIGS. 18B and 18C. The exemplary dental restoration 113D in these figures has functionality of a transfer jig 113C, but does not have a restoration base 113E and does not have any connectors attachable to the simulated fixation element 108 on a model base 201 since the positioning posts 125 on the dental restoration can be aligned and inserted into the recessed holes 128 created on the oral structure 102 as shown in FIG. 18A. The dental restoration 113D may also have back connectors 204B' connectable to the model base 201. After positional index of installed implants are taken, implant analogs 207 can be attached to the implant sleeve 123 separated from the installed implants. Additional implant analogs 207 can be also attached to the restoration connectors 121 on the lingual side of the dental restoration 113D to create threaded model connectors 205 that can be used when a final restoration is being fabricated.

The exemplary model base 201 shown in FIG. 18*b* is digitally designed based on the tomography scan data of patient's oral structure 102 combined with a tub design model base 201. In the model base design, some parts of the oral structure 102 are removed in the area that implant analogs 207 are expected to be positioned. The areas that include positioning holes 128 and that support the rest or rests 124 on the dental restoration 113D are kept as a simulated and modified oral structure 102 and incorporated into the model base 201. The dental restoration 113D can be attached to the model base 201 by connecting its back connectors 204C to the corresponding connectors 204 of the model base 201 and the positioning posts 125 of the dental restoration 113D to the recessed holes 128. A model material 209 can be poured into the tub of the model base 201 to make a master implant model 210. By doing so, the implant analogs 207 attached to the restoration connectors 121 will be included in the master implant model 210 and will become threaded model connectors 205 that can be used with a dental restoration 113D on the master implant model 210.

It is also relevant to note that, by using a dental restoration 113D with a restoration connector 121 to accept additional implant analogs, a postoperative master implant model 210 with the threaded model connectors 205 can be made with any generic model base 201 or mold (without any built-in connectors 204, 204*b*, recessed holes 128 or simulated oral structure 102). In that case, a model material 209 can be poured into the generic model base or mold 201, and the dental restoration 113D with implant analogs 207 attached to the implant sleeve 123 (which are glued to the dental restoration 113D) and the connected implant analog/threaded model connector element 207/205 attached to the restoration connectors 121 can be lowered into the model base 201 before the model material 209 is hardened so that the analogs 207 and connected implant analog/threaded model connector elements 207/205 are partially submerged into the model material 209. After the model material 209 hardens, the dental restoration 113D can be removed from the implant analogs 207 and a postoperative implant model will be created. Though the generic model base/mold 201 itself is not align-able to the preoperative master scan data and design file, the master implant model 210 will become alignable to the preoperative master data and design file after the model is scanned and digitized by using the threaded model connector 205 coordinates as the fiducial markers align with corresponding design coordinates oriented and stored in the preoperative master data file.

Figure 19A:
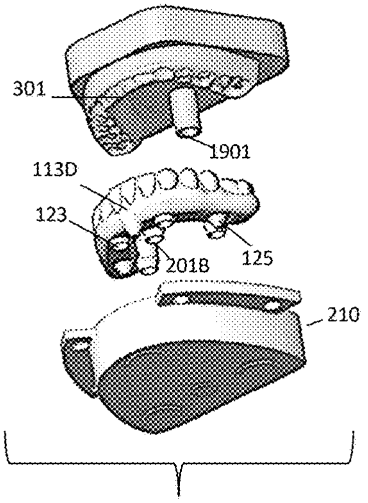
FIG. 19A is a bottom exploded perspective view of an exemplary master implant model, a dental restoration and bite registration assembly.
Figure 19B:
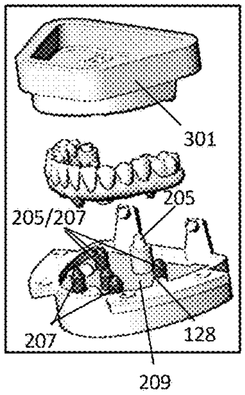
FIG. 19B is a top exploded perspective view of an exemplary master implant model, a dental restoration and bite registration assembly.
Figure 19C:
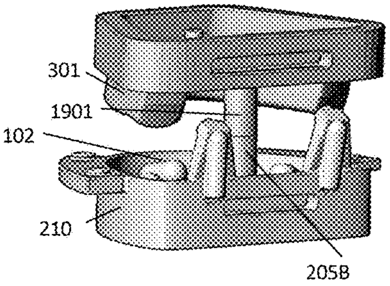
FIG. 19C is a back perspective view of the master implant model and the bite registration assembled.

FIG. 19A is a bottom exploded perspective view of an exemplary master implant model 210, a dental restoration 113D and bite registration assembly 301. FIG. 19B is a top exploded perspective view of an exemplary master implant model 210, a dental restoration 113D and bite registration assembly 301. FIG. 19C is a back perspective view of the master implant model 210 and the bite registration 301 assembled. This exemplary master implant model 210 has a back center connector element 205B connectable to a bite registration connector 1901 on the bite registration model 301 to set the height of occlusion as shown in FIG. 19C. It should be noted that, in this master implant model 210, the recessed holes 128 to accept the positioning posts 125 are in geometrically shaped islands serving the role of oral structure 102.

Figure 20A:
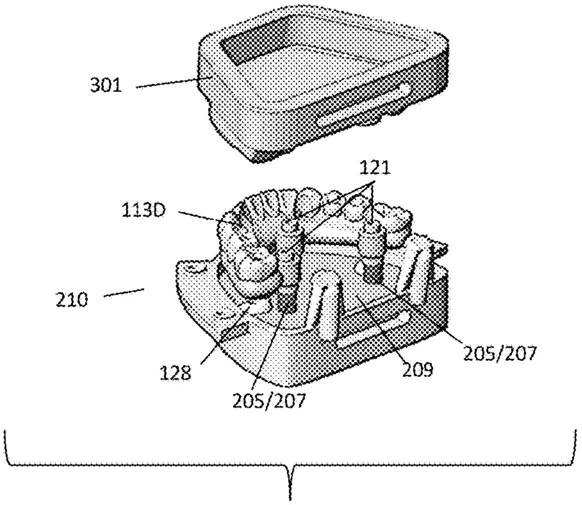
FIG. 20A is a back exploded perspective view of another exemplary master implant model, a dental restoration, and a bite registration model.
Figure 20B:
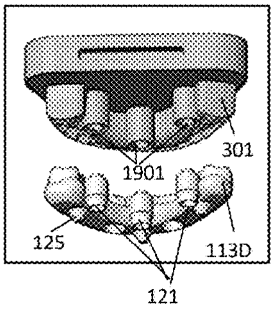
FIG. 20B is an exploded bottom perspective view of the dental restoration and the bite registration model.

FIG. 20A is a back exploded perspective view of another exemplary master implant model 210, a dental restoration 113D, and a bite registration model 301. FIG. 20B is an exploded bottom perspective view of the dental restoration 113D and the bite registration model 301. In these figures, the bite registration connectors 1901 on the bite registration model 301 connect to the restoration connectors 121 and/or threaded model connectors 205 on the dental restoration 113D, and the restoration connectors 121 attach to the threaded restoration connector 205, which may be made with implant analog 207, on the master implant model 210. The restoration connectors 121 on dental restoration 113D can be built into the appliance instead of being held by the threaded model connectors 205 and each part of the assembly may be connectable to one another by other types of connectors without departing from the scope of the present disclosure.

Figure 21A:
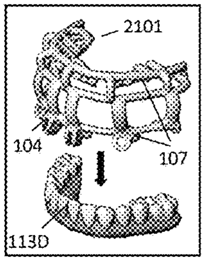
FIG. 21A is an exploded perspective view of a dental restoration with an exemplary cage type dental restoration carrier assembly having fixation connectors above an oral structure with implant parts attached to installed implants.
Figure 21B:
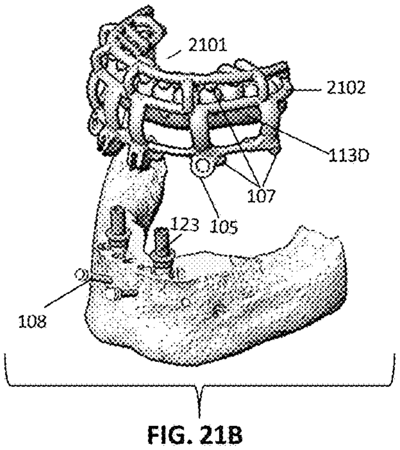
FIG. 21B is an exploded perspective view of the dental restoration and the cage type carrier.
Figure 21C:
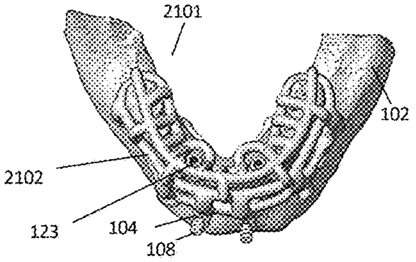
FIG. 21C is a top plan view of the cage type carrier and the dental restoration positioned on the oral structure.
Figure 21D:
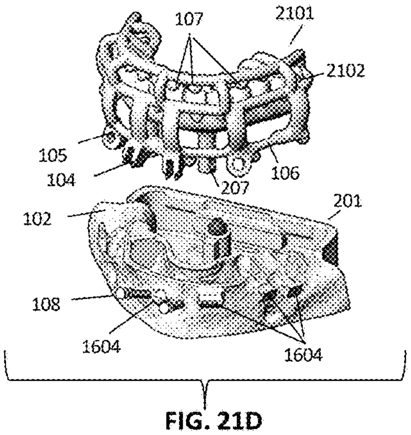
FIG. 21D is an exploded perspective view of the cage type carrier with the dental restoration above a model base with an artificial oral structure.
Figure 21E:
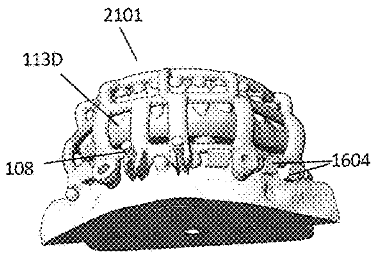
FIG. 21E is a bottom perspective view of the cage type carrier, the dental restoration, and the model base.
Figure 21F:
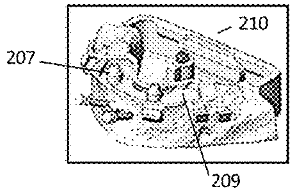
FIG. 21F is a perspective view of a poured implant master model, which includes a model base and an artificial oral structure.

The next set of figures illustrate restoration carriers 2101 that holds a dental restoration 113D from the top. These restoration carriers 2101 can be an alternative to the restoration base 113E described previously. FIG. 21A is an exploded perspective view of a combination dental restoration 113D with an exemplary cage type dental restoration carrier 2101 having fixation connectors 104 above an oral structure 102 with implant sleeves 123 attached to installed implants. FIG. 21B is an exploded perspective view of the dental restoration 113D and the dental restoration carrier 2101. FIG. 21C is a top plan view of the dental restoration carrier 2101 and the dental restoration 113D positioned on the oral structure 102. FIG. 21D is an exploded perspective view of the dental restoration carrier 2101 with the dental restoration 113D above a model base 201 with an artificial oral structure 102. FIG. 21E is a bottom perspective view of the dental restoration carrier 2101, the dental restoration 113D, and the model base 201. FIG. 21F is a perspective view of a poured implant master model 210, which includes an artificial oral structure 102. The dental restoration carriers hold dental restorations 113D in position and maintain the position by clasping the lateral surface of the dental restoration 113D with a cage-like structure that includes a clasp 2102 instead of the adhesive attachment on the bottom used by the restoration base 113E. If the restoration carrier 2101 is used, a dental restoration 113D does not need connectors on its facial surface where aesthetics is important. The restoration carrier 2101 has one or more appliance protrusions 107 to the dental restoration 113D and may have a top support bar with appliance protrusions 107 that fit on the occlusal surface and incisal edge of the dental restoration 113D and multiple vertical support bars that help complete the cage. FIG. 21I and FIG. 21J show restoration carriers 2101 without the top support bar.

If the restoration carrier 2101 is to be attached to one or more fixation elements 108, it has corresponding fixation connectors 104. The restoration carrier 2101 also has a front support bar 106 integral with the clasp 2102, with multiple vertical support bars and one or more application protrusions 107 to abut the oral structure 102. After the implant sleeve 123 are attached to the dental restoration 113D and implant analogs 207 are attached to the implant sleeve 123. If the model base 201 has connectors such as base tabs 1604 and/or simulated fixation element 108 to accept this type of restoration carrier 2101, the assembly of the dental restoration 113D and the restoration carrier 2101 can be transferred and attached to a model base 201 as shown in FIGS. 21D-F to create a master implant model 210.

Figure 21G:
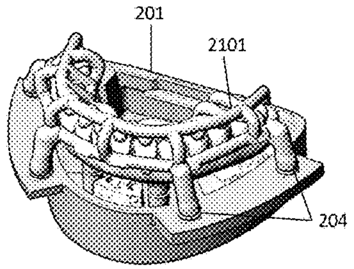
FIG. 21G is a perspective view of a dental restoration and another exemplary cage type carrier with connector legs attached to a model base.
Figure 21H:
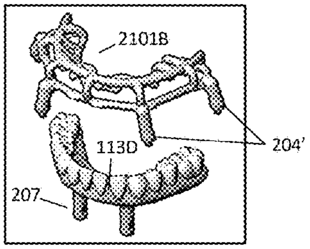
FIG. 21H is an exploded perspective view of the dental restoration and the cage type carrier with connector legs.
Figure 21I:
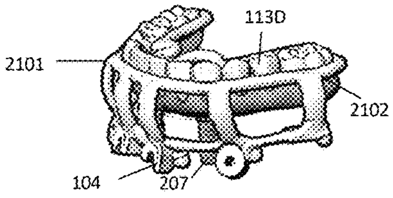
FIG. 21I is a perspective view of an exemplary assembly of a dental restoration and open-top cage type carrier.
Figure 21J:
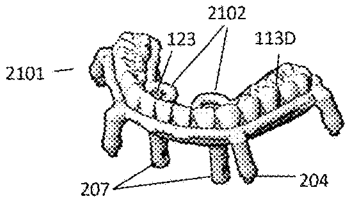
FIG. 21J is a perspective view of an exemplary assembly of a dental restoration and open-top cage type carrier.

FIG. 21G is a perspective view of a dental restoration 113D and another exemplary restoration carrier 2101 with connector legs 204' attached to a model base 201. FIG. 21H is an exploded perspective view of the dental restoration 113D and the restoration carrier 2101 with connector legs 204'. FIG. 21I is a perspective view of an exemplary assembly of a dental restoration 113D and open-top cage type carrier 2101. FIG. 21J is a perspective view of an exemplary assembly of a dental restoration 113D and open-top cage type carrier 2101. If the model base 201 design does not allow the restoration carrier 2101 for the oral structure 102 to fit as shown in FIG. 21F-G, the dental restoration 113D may be attached to a restoration carrier 2101 that has connector legs 204' corresponding with the model connectors 204 on the model base 201. It should be noted that this design for the restoration carrier 2101 can be used for a stackable type of surgical guide set to fit onto a bone reduction jig 113A.

Figure 21K:
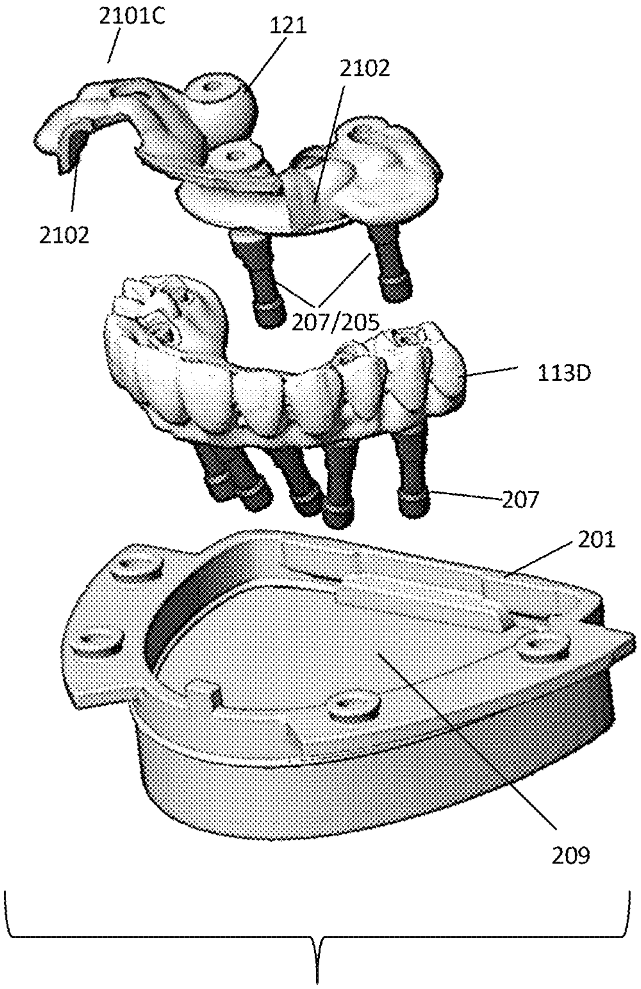
FIG. 21K is an exploded perspective view of an exemplary assembly of a dental restoration and another exemplary restoration carrier above a model base.
Figure 21L:
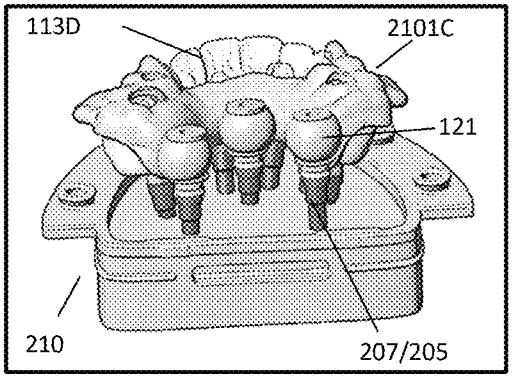
FIG. 21L is a back perspective view of the assembled restoration and the restoration carrier placed on the model base.

FIG. 21K is an exploded perspective view of an exemplary assembly of a dental restoration 113D and a threaded attachment restoration carrier 2101C above a model base 201. FIG. 21L is a back perspective view of the assembled dental restoration 113D and the threaded attachment restoration carrier 2101C placed on the model base 201. This carrier 2101C is similar to the previous carriers 2101, but does not connect directly to a model base 201. The threaded attachment restoration carrier 2101C has multiple threaded restoration connectors 121 that accept implant analogs 207 on its lingual side. The threaded attachment restoration carrier 2101C may have a cage type structure and may utilize clasps 2102 as shown in FIG. 21K. The threaded attachment restoration carrier 2101C is suitable for carrying a dental restoration 113D, like the one shown in this figure. In order to make a postoperative master implant model 210, a model material 209 can be poured into the model base 201, and, while the model material 209 is still soft, the assembled threaded attachment restoration carrier 2101C and dental restoration 113D with implant analogs 207 (as the positional index of installed implants) can be lowered into the model material 209 in the model base 201. The implant analogs/threaded restoration connector elements 207/205 on the threaded attachment restoration carrier 2101C and the implant analogs 207 on the dental restoration 113D are partially submerged into the model material 209. After the model material 209 is hardened, the threaded attachment restoration carrier 2101C and the dental restoration 113D can be removed from the implant analogs 207 and the implant analog/threaded restoration connector elements 207/205. The threaded attachment restoration carrier 2101C and the dental restoration 113D can be separated, and a postoperative implant master model 210 will result. With this method, when the master dental model 210 is scanned to make a digital master implant model, the coordinates of the scanned model base 201 cannot be used to align the positional index of installed implants coordinates to the preoperative master data file that includes preoperative oral scan data and appliance design coordinates since neither the threaded attachment restoration carrier 2101C, nor the dental restoration 113D has connector element connectable to the model base 201 in this example. However, the master implant model 210 itself can become alignable to the pre-operative scan and design data file if the master implant model 210 is scanned. Additionally, a new series of dental appliances 113A-F attachable to the implant analogs/threaded restoration connector elements 207/205 can be designed on the digitized master implant model 210.

Figure 22:
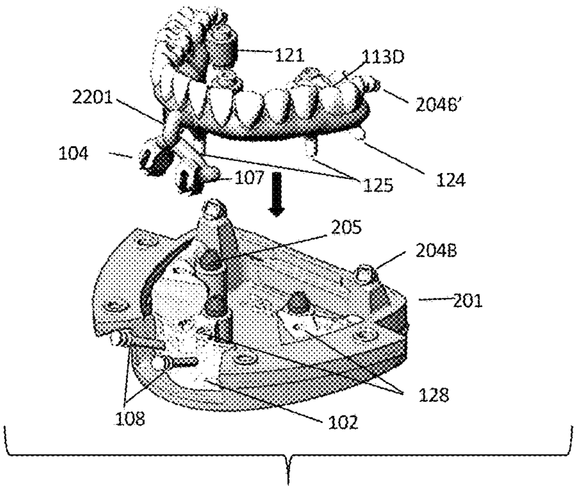
FIG. 22 is an exploded perspective view of an exemplary dental restoration with fixation connectors above an exemplary hybrid dental model base, including an artificial oral structure.

FIG. 22-FIG. 25E show other variations of guide and model parts designs and applications of features. FIG. 22 is an exploded perspective view of an exemplary dental restoration 113D with fixation connectors 104 above an exemplary hybrid dental model base 201, including an artificial oral structure 102. Recessed holes 128 are placed in modified partial oral structure 102 which also has fixation element 108 corresponding with the fixation connectors 104 on a dental restoration 113D. This feature is another alternative to using a model base 201. FIG. 22 also shows exemplary dental restoration 113D that have the corresponding fixation connectors 104 connected by connector arms 2201, the positioning posts 125 corresponding with the positioning holes 128 and the oral structure rests 124 configured to rest on the modified oral structure 102 of the model base 201.

Figure 23:
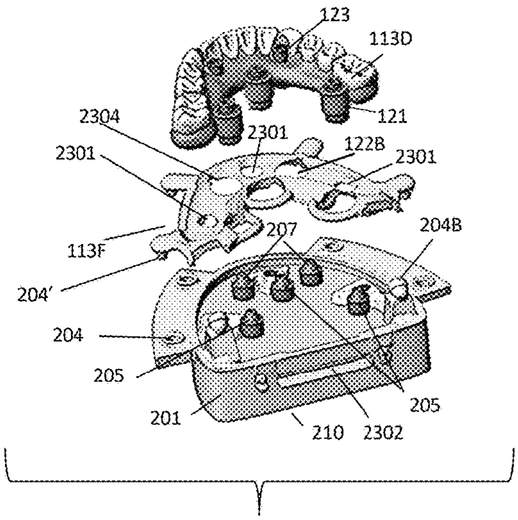
FIG. 23 is an exploded back perspective view of a poured implant model, restoration base with leg connectors and dental restoration.

FIG. 23 is an exploded back perspective view of a poured master implant model 210, timing jig 113F with connector legs 204' and dental restoration 113D. Besides having through holes 122*b* for installed implant parts 207 and implant sleeves (cylinders/copings) 123, the exemplary timing jig 113F shown in FIG. 23 has through-holes 2301 for positioning posts 125 that are on the dental restoration 113D with transfer jig functionality. These features of the timing jig 113F provide it with the additional functionality of a restoration base 113E. This timing jig 113F has connector legs 204' attachable to the corresponding connectors 204 on the model base 201. The timing jig 113F is compatible for use with the model base 201 or the patient's oral structure 102 if the guide set is stackable and its connector legs 204' are attachable to the connectors 204 on the bone reduction jig 113A. Additionally, the exemplary timing jig 113F can be temporarily glued to the dental restoration 113D, although it would then cease to function as a timing jig 113F and strictly become usable as a restoration base 113E. The timing jig 113F needs to be detachably attachable to the dental restoration 113D to serve the function of a timing jig. The timing jig 113F is identifiable with its placement of one or more timing markers 2304 on or next to the through holes 122*b* for aligning timing marks on implant parts 207 or implant abutments. It should be noted that a timing jig 113F with one or more fixation connectors 104 is defined by being detachably attachable to a dental restoration 113D and having timing markers 2304. Moreover, instead of the dental restoration 113D having one or more restoration connectors 121 to accept extra implant analog/threaded restoration connector element(s) 207/205 on the lingual side, the timing jig 113F may have the restoration connector 121.

Figure 24:
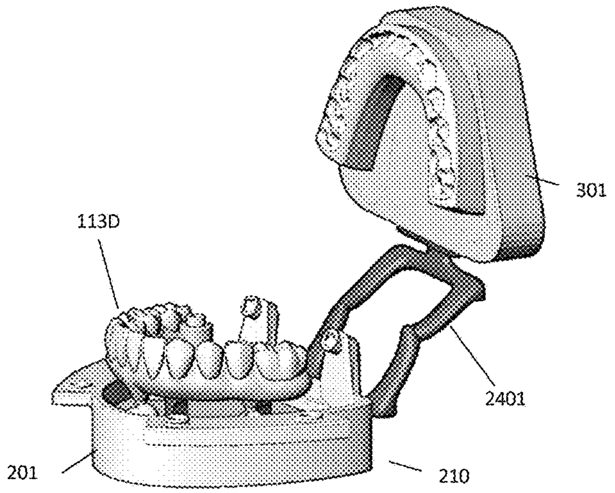
FIG. 24 is a perspective view of articulated dental implant model with a dental restoration positioned on the model.

FIG. 24 is a perspective view of articulated dental master implant model 210 with a dental restoration 113D positioned on the model base 201. FIG. 24 shows the master implant model 210 articulated by an articulator 2401 which can be attached to a back slot 2302 (shown in FIG. 23) of the model base 201 and to the one on the bite restoration model 301 or opposing model. The articulator 2401 allows the bite restoration model to move into abutment with the dental restoration 113D and move away from the dental restoration without disconnecting the bite restoration model 301 from the model base 201.

Figure 25A:
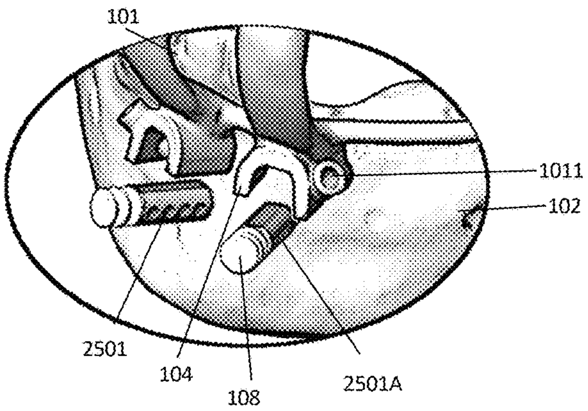
FIG. 25A is a partial perspective view of an exemplary scan marker drill guide sleeves fixed to an oral structure with fixation elements.
Figure 25B:
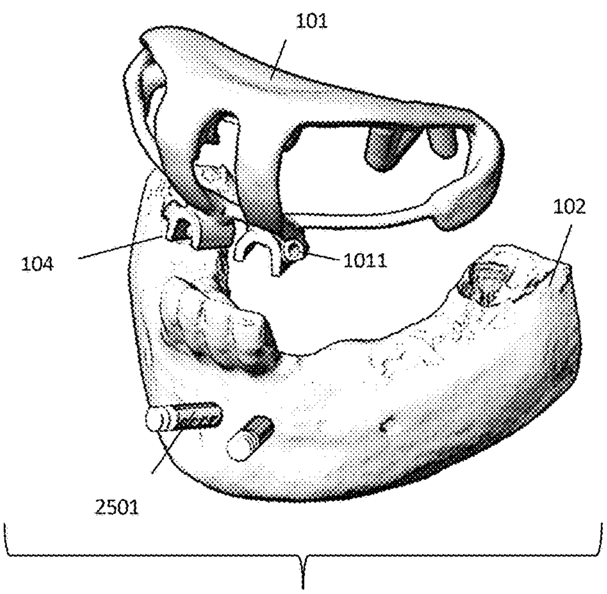
FIG. 25B is a perspective view of an exemplary scan marker drill guide sleeves fixed to an oral structure with fixation elements.
Figure 25C:
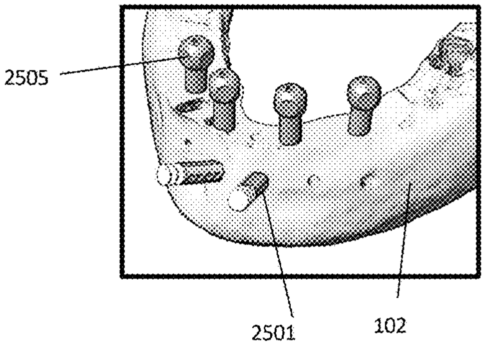
FIG. 25C is a partial perspective view of an exemplary scan marker drill guide sleeves fixed to an oral structure with fixation elements.

FIG. 25A is a partial perspective view of an exemplary scan marker drill guide sleeves 2501 fixated to an oral structure 102 with fixation elements 108. FIG. 25B is an exploded perspective view of a fixation site drill guide 101 and exemplary scan marker drill guide sleeves 2501 fixated to an oral structure 102 with fixation elements 108. FIG. 25C is a partial perspective view of an exemplary scan marker drill guide sleeves 2501 fixated to an oral structure 102 with fixation elements 108. Guiding passages 1011 provide means to lock engagement of the fixed site drill guide 101 to the fixation connectors 104 with the locking pins 1009. The drill guide sleeve fiducial marker 2501 is a tube that has a drill guide opening 105 that snugly fits to fixation element 108. The scan marker drill guide sleeves 2501 can have a mostly cylindrical outer surface but need to have some flat outer surface area (or areas) where it is configured to contact an inner surface of the corresponding fixation connector 104 to prevent the drill guide fiducial marker 2501 from rotating around the fixation element 108 and corresponding fixation connector 104 may have a matching flat inner surface area. If used as a fiducial marker, the scan marker drill guide sleeves 2501 may also have distinctive markings on its outer surface.

To place the scan marker drill guide sleeves 2501 on an oral structure 102: (1) Attach the scan marker drill guide sleeves 2501 to the fixation connector 104 on a fixation site drill guide 101 by inserting a locking pin 1009 into the guiding passage 1011; (2) Position the fixation site drill guide 101 on the patient's oral structure 102; (3) Drill a fixation site on the oral structure 102 through the drill guide opening 105 of the scan marker drill guide sleeves 2501; (4) Insert a fixation element 108 through the drill guide opening 105; and (5) Remove the locking pin 1009 and remove the fixation drill guide 101. Since the scan marker drill guide sleeve 2501 stays on the fixation element 108, subsequent dental appliances 113A-F will have corresponding fixation connectors 104 that fit onto the scan marker drill guide sleeves 2501 instead of the fixation elements 108. It should be noted that other types of locking parts, such as the locking rings 1001, can be used to lock this type of scan marker drill guide sleeves 2501 to a fixation connector 104.

The scan marker drill guide sleeves 2501 can be used as a scan marker to align the digital positional index of installed implants to the preoperative scan data. The following scans should be taken: (1) a scan of the oral structure 102 including the scan marker drill guide sleeves 2501 before making significant changes to the oral structure 102, (2) another scan of the oral structure 102 after implants are installed with the scan marker drill guide sleeves 2501 and scan bodies 2505 attached to the installed implants as shown in FIG. 25C. As previously explained in [Method 4], digital positional index of installed implants can be aligned to the preoperative scan data file by aligning coordinates of the unchanged and visible part of the oral structure 102 (such as existing teeth) on the first scan data to the coordinates of the same oral structure 102 on preoperative scan data. Then, the second scan data can be aligned to the preoperative scan data by aligning the coordinates of the scan marker drill guide sleeves 2501 on the second scan data to the ones on the first set of scan data already aligned to the preoperative scan data.

Figure 25D:
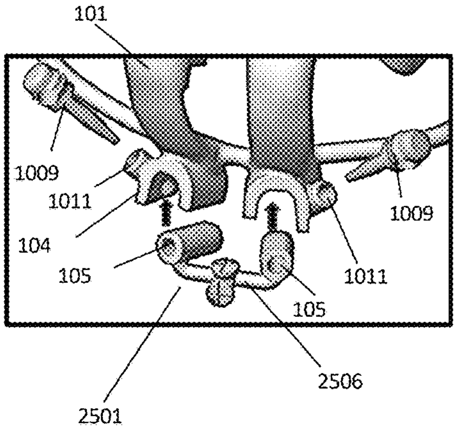
FIG. 25D is a partial perspective view of assemblies of an exemplary scan marker drill guide sleeve, a fixation site drill guide with fixation connectors and locking pins.
Figure 25E:
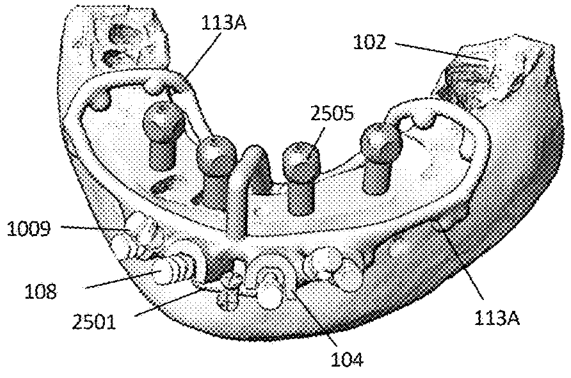
FIG. 25E is a perspective view of the scan marker drill guide sleeve fixed to an oral structure with fixation elements and locked to a bone reduction jig with locking pins.

FIG. 25D is a partial perspective view of assemblies of an exemplary scan marker drill guide sleeve 2501, a fixation site drill guide 101 with fixation connectors 104 and locking pins 1009. FIG. 25E is a perspective view of the scan marker drill guide sleeve 2501 fixed to an oral structure 102 with fixation elements 108 and locked to a bone reduction jig 113A with locking pins 1009. In this design, multiple (usually two) tubes with drill guide openings 105 are connected by an arm 2506. Though this scan marker drill guide sleeves 2501 may also have scan markers on the cylindrical surfaces of the tube portions, it can have one or more scan markers on the connector arm 2506. If one or more scan markers are placed on the connector arm 2506, a dental appliance 101, 113A-F locked to on an oral structure 102 can be included in the scan without hiding the scan marker on the scan marker drill guide sleeves 2501 as shown in FIG. 25E with scan bodies 2505 and a bone reduction jig 113A in place. Additionally, this type of scan marker drill guide sleeves 2501 does not have to have any flat outer surfaces configured to contact the inner surface of the corresponding fixation connectors since the scan marker drill guide sleeves 2501 are not rotatable in an engaged position. This scan marker drill guide sleeves 2501 can be locked to fixation connectors 104 with other types of locking parts such as locking rings 1001 with previously described structure.

This scan marker drill guide sleeves 2501 can be locked to the fixation connectors 104 of the fixation site drill guide 101 by inserting locking pins 1009 into the guide passages 1011 on the fixation connectors 104 as shown. Then, fixation sites can be drilled through the drill guide openings 105, and, after fixation elements 108 are inserted, the fixation site drill guide 101 can be removed, but the scan marker drill guide sleeves 2501 will stay attached to the fixation elements 108 during the subsequent surgical procedure. If the scan marker drill guide sleeves 2501 is used as a scan marker, the same steps can be taken as previously explained. It should be noted that the previously mentioned various designs and features (such as locking systems) of drill guide set can be mixed and matched to be applied to various types of guide set appliances.

What is claimed is:

1. A dental surgical guide set comprising:
- at least one fixation element, wherein each of the at least one fixation element is independently capable of fixation to an oral structure;
- a dental appliance comprising at least one fixation connector integral therewith and removably engageable with the at least one fixation element after the at least one fixation element is fixed to the oral structure, whereby engagement of the at least one fixation element and the at least one fixation connector fixes the dental appliance against the oral structure; and
- a fixation site drill guide temporarily mounted to the oral structure to form at least one hole for the at least one fixation element, wherein the dental appliance further comprises at least one of: a bone reduction jig; a surgical drill guide; a transfer jig; a dental restoration; a restoration base; a restoration carrier; a timing jig; and a scan appliance.

2. The dental surgical guide set of claim 1, further comprising at least one locking ring removably engaged to the at least one fixation element and the dental appliance at the at least one fixation connector.

3. The dental surgical guide set of claim 2, wherein the at least one locking ring is a drill guide sleeve.

4. The dental surgical guide set of claim 2, wherein at least one of a drill guide sleeve or the at least one locking ring further comprises a locking bolt engageable with the at least one fixation connector.

5. The dental surgical guide set of claim 1, further comprising a plurality of removably attachable drill guide sleeves independently connected to each other and removably engaged with the at least one fixation connector.

6. The dental surgical guide set of claim 1, further comprising a drill guide sleeve engaged with the at least one fixation connector, the drill guide sleeve comprising a scan marker.

7. The dental surgical guide set of claim 1, wherein the at least one fixation element further comprises a rotatable locking bolt, wherein rotation of the rotatable locking bolt moves the rotatable locking bolt between an engaged and disengaged position.

8. The dental surgical guide set of claim 7, wherein the at least one fixation connector further comprises a recess positioned to receive the rotatable locking bolt when the rotatable locking bolt is in the engaged position; and wherein the locking bolt is removably engageable with the at least one fixation element.

9. The dental surgical guide of claim 1, further comprising a model base, wherein the dental appliance is connectable to the model base.

10. The dental surgical guide set of claim 1, wherein the at least one fixation connector further comprises a horseshoe-shaped cavity sized to receive the at least one fixation element within the horseshoe-shaped cavity when the dental appliance is positioned against the oral structure.

11. The dental surgical guide set of claim 10, further comprising a drilling guide sleeve having two ribs, wherein the drilling guide sleeve snap fits within the horseshoe-shaped cavity at a channel between the two ribs.

12. The dental surgical guide set of claim 1, wherein the dental appliance further comprises at least one of: a model connector connectable to a model base; and at least one connector capable of holding a detachably attachable part configured to form a post-operative model connector.

13. The dental surgical guide set of claim 1, further comprising a locking pin, wherein the dental appliance further comprises a locking passage integrally formed therein, and wherein the at least one fixation element and the at least one fixation connector are engaged and the locking pin is positioned in the locking passage abutting the at least one fixation element thereby removably locking the engagement of the at least one fixation element and the at least one fixation connector.

14. The dental surgical guide set of claim 1, further comprising a midsection protrusion on at least one of:

a fixation element of the at least one fixation element between a fixation stem and a fixation distal end, and a drill guide sleeve between a proximate end and a distal end of the drill guide sleeve, wherein a diameter of the midsection protrusion is greater than a diameter of the fixation stem or a diameter of the proximate end of the drill guide sleeve, and wherein the at least one fixation connector further comprises a C-shaped entrance opening sized to receive the midsection protrusion and a stop opening smaller than the midsection protrusion or the drill guide sleeve proximate end, whereby a distance between each end of the C-shape is smaller than the diameter of the midsection protrusion inhibiting lifting of the oral structure.

15. The dental surgical guide set of claim 1, wherein the at least one fixation element further comprises a self-tapping screw for drilling the at least one hole.

16. A dental surgical guide set comprising:

at least one fixation element, wherein each of the at least one fixation element is independently capable of fixation to an oral structure;

a dental appliance comprising at least one fixation connector integral therewith and removably engageable with the at least one fixation element after the at least one fixation element is fixed to the oral structure, whereby engagement of the at least one fixation element and the at least one fixation connector fixes the dental appliance against the oral structure;

at least one locking ring removably engaged to the at least one fixation element and the dental appliance at the at least one fixation connector; and wherein the at least one locking ring is a drill guide sleeve.

17. A dental surgical guide set comprising:

at least one fixation element, wherein each of the at least one fixation element is independently capable of fixation to an oral structure;

a dental appliance comprising at least one fixation connector integral therewith and removably engageable with the at least one fixation element after the at least one fixation element is fixed to the oral structure, whereby engagement of the at least one fixation element and the at least one fixation connector fixes the dental appliance against the oral structure; and a drill guide sleeve engaged with the at least one fixation connector, the drill guide sleeve comprising a scan marker.

18. A dental surgical guide set comprising:

at least one fixation element, wherein each of the at least one fixation element is independently capable of fixation to an oral structure;

a dental appliance comprising at least one fixation connector integral therewith and removably engageable with the at least one fixation element after the at least one fixation element is fixed to the oral structure, whereby engagement of the at least one fixation element and the at least one fixation connector fixes the dental appliance against the oral structure;

wherein the at least one fixation element further comprises a rotatable locking bolt, wherein rotation of the rotatable locking bolt moves the rotatable locking bolt between an engaged and disengaged position; and wherein the at least one fixation connector further comprises a recess positioned to receive the rotatable locking bolt when the rotatable locking bolt is in the engaged position; and wherein the locking bolt is removably engageable with the at least one fixation element.

19. A dental surgical guide set comprising:

at least one fixation element, wherein each of the at least one fixation element is independently capable of fixation to an oral structure;

a dental appliance comprising at least one fixation connector integral therewith and removably engageable with the at least one fixation element after the at least one fixation element is fixed to the oral structure, whereby engagement of the at least one fixation element and the at least one fixation connector fixes the dental appliance against the oral structure;

wherein the at least one fixation connector further comprises a horseshoe-shaped cavity sized to receive the at least one fixation element within the horseshoe-shaped cavity when the dental appliance is positioned against the oral structure; and a drilling guide sleeve having two ribs, wherein the drilling guide sleeve snap fits within the horseshoe-shaped cavity at a channel between the two ribs.

20. A dental surgical guide set comprising:

at least one fixation element, wherein each of the at least one fixation element is independently capable of fixation to an oral structure;

a dental appliance comprising at least one fixation connector integral therewith and removably engageable with the at least one fixation element after the at least one fixation element is fixed to the oral structure, whereby engagement of the at least one fixation element and the at least one fixation connector fixes the dental appliance against the oral structure;

a midsection protrusion on at least one of:

a fixation element of the at least one fixation element between a fixation stem and a fixation distal end, and a drill guide sleeve between a proximate end and a distal end of the drill guide sleeve, wherein a diameter of the midsection protrusion is greater than a diameter of the fixation stem or a diameter of the proximate end of the drill guide sleeve, and wherein the at least one fixation connector further comprises a C-shaped entrance opening sized to receive the midsection protrusion and a stop opening smaller than the midsection protrusion or the drill guide sleeve proximate end, whereby a distance between each end of the C-shape is smaller than the diameter of the midsection protrusion inhibiting lifting of the oral structure.

* * * * *